United States Patent
Sloan

(10) Patent No.: US 12,011,408 B2
(45) Date of Patent: Jun. 18, 2024

(54) CONTROL OF SEXUAL STIMULATION DEVICES USING MOTION-SENSING CONTROLLERS

(71) Applicant: Brian Sloan, Mercer Island, WA (US)

(72) Inventor: Brian Sloan, Mercer Island, WA (US)

( * ) Notice: Subject to any disclaimer, the term of this patent is extended or adjusted under 35 U.S.C. 154(b) by 14 days.

(21) Appl. No.: 17/853,284

(22) Filed: Jun. 29, 2022

(65) Prior Publication Data

US 2022/0323292 A1 Oct. 13, 2022

Related U.S. Application Data

(63) Continuation-in-part of application No. 16/934,566, filed on Jul. 21, 2020, now Pat. No. Re. 49,249, which (Continued)

(51) Int. Cl.

| | | |
|---|---|---|
| *A61F 5/00* | (2006.01) | |
| *A61F 5/41* | (2006.01) | |
| *A61H 1/00* | (2006.01) | |
| *A61H 7/00* | (2006.01) | |
| *A61H 19/00* | (2006.01) | |

(Continued)

(52) U.S. Cl.
CPC ............... *A61H 19/32* (2013.01); *A61F 5/41* (2013.01); *A61H 1/00* (2013.01); *A61H 7/001* (2013.01); *A61H 7/005* (2013.01); *A61H 7/008* (2013.01); *A61H 19/44* (2013.01); *A61H 23/006* (2013.01); *A61H 23/02* (2013.01); *A61F 2005/411* (2013.01); *A61F 2005/412* (2013.01); *A61F 2005/417* (2013.01); *A61H 23/0254* (2013.01); *A61H 2201/0153* (2013.01); *A61H 2201/0157* (2013.01); *A61H 2201/0207* (2013.01); *A61H 2201/0221* (2013.01); *A61H 2201/10* (2013.01); *A61H 2201/123* (2013.01); *A61H 2201/1472* (2013.01); *A61H 2201/149* (2013.01); *A61H 2201/163* (2013.01); *A61H 2201/1642* (2013.01); *A61H 2201/165* (2013.01); *A61H 2201/1664* (2013.01);

(Continued)

(58) Field of Classification Search
CPC .... A61H 19/44; A61H 19/32; A61H 23/0254; A61H 2201/165; A61H 2201/1635; A61H 2201/501; A61H 2201/5043; A61H 2201/5061; A61H 2201/149; A61H 2201/5071; A61H 2201/5084; A61H 2201/5092; A61H 2201/5097
See application file for complete search history.

(56) References Cited

U.S. PATENT DOCUMENTS 6,902,525 B1 * 6/2005 Jewell .................... A61H 19/44
600/38
10,143,618 B2 12/2018 Cambridge (Continued)

*Primary Examiner* — Catherine S Williams
(74) *Attorney, Agent, or Firm* — Boon Intellectual Property Law, PLLC; Brian S. Boon

(57) ABSTRACT

A system and method for controlling sexual stimulation devices using motion-sensing controllers. The system comprises a male sexual stimulation device and a motion sensing controller configured to control the operation of the reciprocating linear motion driver. In operation, natural motions of a user with the motion sensing controller result in corresponding motions of the male sexual stimulation device such as reciprocal linear motions and rotational motions.

7 Claims, 30 Drawing Sheets

Related U.S. Application Data is an application for the reissue of Pat. No. 10,492,983, which is a continuation-in-part of application No. 16/373,529, filed on Apr. 2, 2019, now Pat. No. 10,492,982, which is a continuation of application No. 16/045,705, filed on Jul. 25, 2018, now Pat. No. 10,272,011.

(60) Provisional application No. 62/655,712, filed on Apr. 10, 2018.

(51) Int. Cl.
*A61H 23/00* (2006.01)
*A61H 23/02* (2006.01)

(52) U.S. Cl.
CPC .. *A61H 2201/1669* (2013.01); *A61H 2201/50* (2013.01); *A61H 2201/5023* (2013.01); *A61H 2205/087* (2013.01)

(56) References Cited

U.S. PATENT DOCUMENTS

| | | | |
|---|---|---|---|
| 10,576,013 B1 * | 3/2020 | Sloan | G06T 7/251 |
| 10,638,174 B2 * | 4/2020 | Sloan | H04N 21/47815 |
| 2013/0281776 A1 | 10/2013 | Levy | |
| 2014/0243590 A1 * | 8/2014 | Fang | A61H 23/02 600/38 |
| 2015/0328082 A1 * | 11/2015 | Jiang | A61H 23/02 600/38 |
| 2019/0167514 A1 | 6/2019 | Cooper et al. | |
| 2020/0253816 A1 * | 8/2020 | Sloan | G06N 3/0454 |

* cited by examiner

CONTROL OF SEXUAL STIMULATION DEVICES USING MOTION-SENSING CONTROLLERS

CROSS-REFERENCE TO RELATED APPLICATIONS

Priority is claimed in the application data sheet to the following patents or patent applications, the entire written description of each of which is expressly incorporated herein by reference in its entirety:
Ser. No. 16/934,566
Ser. No. 16/528,334
Ser. No. 16/373,529
Ser. No. 16/045,705
62/655,712

BACKGROUND

Field of the Art

The present invention is in the field of computer control systems, and more specifically the field of control systems for sexual stimulation devices.

Discussion of the State of the Art

In the field of sexual stimulation devices, control systems are typically limited to on-device controls with buttons, dials, or sliders which allow the user to change settings in discrete steps. Such controls can be awkward to manipulate during use of the device, interrupting the user's experience, and do not represent a natural association of the control with the actions of the device.

What is needed is a means of controlling sexual stimulation devices that relies on natural movements associated with the actions of the device.

SUMMARY

Accordingly, the inventor has conceived, and reduced to practice, a system and method for controlling sexual stimulation devices using motion-sensing controllers. The system comprises a male sexual stimulation device and a motion sensing controller configured to control the operation of the reciprocating linear motion driver. In operation, natural motions of a user with the motion sensing controller result in corresponding motions of the male sexual stimulation device such as reciprocal linear motions and rotational motions.

According to a preferred embodiment, a male sexual stimulation system is disclosed, comprising: a male sexual stimulation device comprising: a first computing device comprising a first processor, a first memory, and a wireless receiver; a reciprocating linear motion driver; a gripper attached to the reciprocating linear motion driver; and a flexible sleeve which is inserted into the gripper and which has a means for affixing the sleeve to the gripper; and a motion sensing controller configured to control the operation of the reciprocating linear motion driver, comprising: a second computing device comprising a second processor, a second memory, and a wireless transmitter; and a motion sensor.

According to an aspect of an embodiment, the controller is moved in a reciprocal linear motion, the motion is detected by the motion sensor and a control signal corresponding to the motion is transmitted by the wireless transmitter to the wireless receiver, and the first computing device operates the reciprocating linear motion driver in accordance with the control signal.

According to an aspect of an embodiment, the controller is moved in a reciprocal linear motion, the motion is detected by the motion sensor and motion data corresponding to the motion is transmitted by the wireless transmitter to the wireless receiver, and the first computing device converts the motion data into a control signal corresponding to the motion and operates the reciprocating linear motion driver in accordance with the control signal.

According to an aspect of an embodiment, the system further comprises a second motor, actuator, or driver attached to the gripper mechanism and configured to rotate the gripper about a longitudinal axis parallel to the linear motion independently of the linear motion, wherein when the controller is moved in a rotating motion about a longitudinal axis of the controller, the rotating motion is detected by the motion sensor and a control signal corresponding to the rotating motion is transmitted by the wireless transmitter to the wireless receiver, and the first computing device operates the rotational motor, actuator, or rack and pinion mechanism in accordance with the control signal.

According to an aspect of an embodiment, the system further comprises a second motor, actuator, or driver attached to the gripper mechanism and configured to rotate the gripper about a longitudinal axis parallel to the linear motion independently of the linear motion, wherein when the controller is moved in a rotating motion about a longitudinal axis of the controller, the rotating motion is detected by the motion sensor and motion data corresponding to the motion is transmitted by the wireless transmitter to the wireless receiver, and the first computing device converts the motion data into a control signal corresponding to the rotating motion and operates the rotational motor, actuator, or rack and pinion mechanism in accordance with the control signal.

According to an aspect of an embodiment, the system further comprises: one or more guide rods that guide the linear motion; a pivot or joint installed at one end of the one or more guide rods; and a second motor, driver, or actuator which changes the pivot angle of the one or more guide rods independently of the linear motion; wherein the linear motion driver is affixed to the guide rods such that the linear motion remains parallel to the guide rods as the guide rods tilt; and when the controller is moved in a rotating motion away from a longitudinal axis of the controller, the rotating motion is detected by the motion sensor and a control signal corresponding to the rotating motion is transmitted by the wireless transmitter to the wireless receiver, and the first computing device operates the second motor, driver, or actuator in accordance with the control signal.

According to an aspect of an embodiment, the system further comprises: one or more guide rods that guide the linear motion; a pivot or joint installed at one end of the one or more guide rods; and a second motor, driver, or actuator which changes the pivot angle of the one or more guide rods independently of the linear motion; wherein the linear motion driver is affixed to the guide rods such that the linear motion remains parallel to the guide rods as the guide rods tilt; and when the controller is moved in a rotating motion away from a longitudinal axis of the controller, the rotating motion is detected by the motion sensor and motion data corresponding to the rotating motion is transmitted by the wireless transmitter to the wireless receiver, and the first computing device converts the motion data into a control signal corresponding to the rotating motion and operates the second motor, driver, or actuator in accordance with the control signal.

BRIEF DESCRIPTION OF THE DRAWING FIGURES

The accompanying drawings illustrate several aspects and, together with the description, serve to explain the principles of the invention according to the aspects. It will be appreciated by one skilled in the art that the particular arrangements illustrated in the drawings are merely exemplary, and are not to be considered as limiting of the scope of the invention or the claims herein in any way.

FIG. 31 is a block diagram illustrating an exemplary logical architecture for a client device.

DETAILED DESCRIPTION

Figure 1:
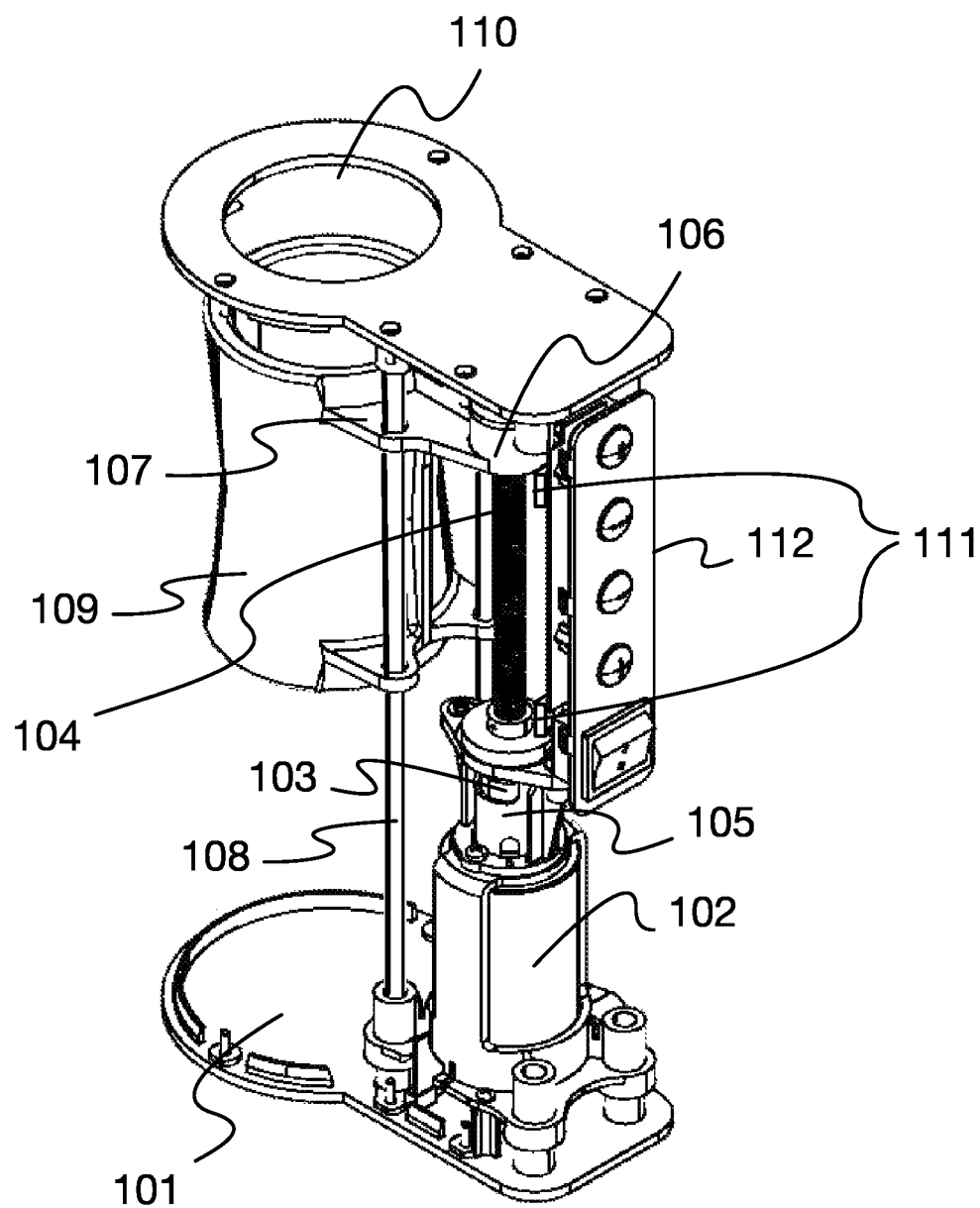
FIG. 1 shows the internal workings of an exemplary male sexual stimulation device according to a preferred embodiment.

The inventor has conceived, and reduced to practice, a system and method for controlling sexual stimulation devices using motion-sensing controllers. The system comprises a male sexual stimulation device and a motion sensing controller configured to control the operation of the reciprocating linear motion driver. In operation, natural motions of a user with the motion sensing controller result in corresponding motions of the male sexual stimulation device such as reciprocal linear motions and rotational motions.

Various embodiments of motion sensing controllers are described herein. In some embodiments, motion sensing controller comprises a cylindrical shaft mounted to a base, wherein sensors in the shaft detect the location of a body part allowing for detection of reciprocal linear motions and rotational motions about the longitudinal axis of the shaft, which are translated into corresponding movements in the sexual stimulation device. In other embodiments, motion sensing controller comprises accelerometers, gyroscopes, and/or magnetometers, allowing for three-dimensional movements in space, which are translated into corresponding movements in the sexual stimulation device.

The mechanisms by which stimulation is provided in male sexual stimulation devices generally fall into one of five basic types: flexible sheath mechanisms, vibratory mechanisms, suction mechanisms, constriction mechanisms, and direct electrical stimulation mechanisms. Each of these devices has at least one significant disadvantage that is overcome by the present invention.

The sheath type device is tube-shaped device made of thermoplastic elastomer, thermoplastic rubber, silicone or other soft, flexible material, with or without an enclosing shell, into which the penis is inserted. The entire sheath device is moved up and down the shaft of the penis, causing stimulation by the friction and pressure of the sheath against the penis. Sheath type devices are used manually, requiring significant user effort, and possibly repetitive strain injury. They use a condom-like sleeve which can slip while in use, and either stretch, compress, or even slip off entirely and become lodged in the sheath. Sheath type devices expose the majority of the penis as the device is moved up and down the shaft of the penis, increasing the likelihood of release of bodily fluids outside of the device. Release of fluids outside of the device creates health and safety dangers to the user and others, can contaminate or damage other surfaces and materials onto which the fluids leak, and can make cleaning of the device itself difficult.

Vibratory mechanisms cause stimulation through oscillatory vibrations, usually created by an electric motor with an offset weight on the motor shaft. In many examples of vibratory mechanisms, for example the Hitachi Wand vibrator, the mechanism is simply pressed against the penis, causing stimulation by transmitting the vibration to the penis. In some forms of the vibratory mechanism, the penis may be inserted into the vibratory mechanism. Vibratory type devices provide a non-ideal type of stimulation, substituting vibration for the reciprocal linear motion of sexual intercourse. Further, most vibratory devices do not enclose the penis, and thus do not possess any method for containing bodily fluids. Vibratory mechanisms, in particular, also tend to produce substantial noise. While they sometimes allow the user to select different vibration patterns, such patterns do not provide much variance in stimulation, as they simply turn the device on and off at specified intervals.

Suction type devices are typically hard plastic tubes into which the penis is inserted at one end, and a suction pump is affixed to the other end. Suction type devices provide no direct stimulation through pressure or friction against the penis, and therefore provide substantially less than ideal stimulation. Suction devices may be combined with a sheath type mechanism.

A constriction type device is one in which the penis is inserted, and a set of rings either restrict blood flow back to the body, enhancing erection, or otherwise put inward radial pressure on the penis. Constriction type devices provide a non-ideal type of stimulation, substituting a squeezing motion for the reciprocal linear motion of sexual intercourse. Further, many constriction type devices do not enclose the penis, and thus do not possess any method for containing bodily fluids.

A direct electrical stimulation device is one in which the penis is stimulated through moderate voltage, very low current electrical shock. The electric shock stimulates nerve endings in the penis and may cause muscle contractions in surrounding tissue. The stimulation may be pulsed to provide different stimulation patterns. Direct electrical stimulation type devices provide a non-ideal type of stimulation, substituting electric shock pulses for the reciprocal linear motion of sexual intercourse. Further, most direction electrical stimulation type devices do not enclose the penis, and thus do not possess any method for containing bodily fluids.

The present invention overcomes the deficiencies in other mechanisms by providing ideal stimulation, similar in pressure and motion to that obtained during sexual intercourse or oral sex, in a device where the user can control the speed, pattern, and location of the motion, and where the penis remains enclosed in a hygienic sheath during stimulation. This device is substantially quieter than many of the alternatives, and provides substantially different stimulation in each of its user-selectable modes or patterns by allowing the user to choose where the stimulation should occur, how often it should occur at selected locations, and how fast it should occur at those locations.

The stimulation device may be controlled by an integrated circuit (IC) built into the device which controls the operation of the motor and monitors any sensors in the device. The IC may be pre-programmed or may, through a universal serial bus (USB) or other interface, be user programmable using a computer application. In either case, the IC may control the operation of the device by adjusting motor speed and direction to implement the patterns of stimulation programmed into the IC. Sensors in the device may be used to set limits of motion of the nut and screw mechanism, to ensure that the mechanism is at one end of its range of motion prior to operation, or to detect and protect against other device parameters such as motor over-heating. Sensors may be of any type suitable for the purpose, including but not limited to electrical contacts, magnetic sensors, magnetic reed switches, mechanical switches, rotational sensors, optical sensors, and temperature sensors.

In an embodiment, the rotary motion from a small electric motor is translated to a linear motion through the use of a screw shaft and nut. The linear motion is translated into penile stimulation by a gripper that provides pressure against the penis through the sleeve as it glides up and down the shaft of the penis. Bodily fluids are contained within a flexible sheath inserted into the gripper, and into which the penis is inserted during use. This differs from sheath type devices in that the penis remains fully inserted in the device while in use, and the device itself is not drawn up and down the penis as with sheath type devices.

In some embodiments, the linear motion may be provided by other linear motion mechanisms. A non-exhaustive list of linear motion mechanisms that could be used in certain embodiments includes: ball screw mechanism, belt-drive linear actuator, linear motor, slider-crank mechanism, and hydraulic or pneumatic linear actuator. The use of these other linear motion mechanisms in certain embodiments will be described herein. Generally speaking, any mechanism capable of generating a linear motion could be used.

In some embodiments, the gripper mechanism may take a variety of alternate forms. A non-exhaustive list of alternative gripper mechanisms that could be used in certain embodiments includes: tubular gripper, annular (ring) gripper, partial-tube or partial-ring gripper, loop or band gripper (including loops and bands made of wire, plastic, metal, or other materials, and including multiple loops or bands), magnetic gripper, gripper with built-in heating elements, inflatable gripper, and vibrating gripper, a gripper with leaf springs or flexible plastic tines. The use of these other gripper mechanisms in certain embodiments will be described herein. It is important to note that the gripper is not limited to mechanisms or structures that "grip" by providing radial inward pressure (for example, leaf springs or flexible plastic tines), although such structures can be used. Generally speaking, any mechanism or structure to which a flexible sleeve may be affixed and which is capable of providing friction against a penis during linear motion may be used as a gripper.

In some embodiments, the linear motion may be augmented with a rotational motion of the gripper. For example, the guide rods supporting the gripper along which the linear motion occurs could be tilted or configured in a spiral, such that each travel along the guide rods causes the gripper to partially rotate about a longitudinal axis parallel to the linear motion. Alternatively, a motor or actuator could be attached to the gripper mechanism to rotate the gripper about a longitudinal axis parallel to the linear motion as it travels in a linear motion.

In some embodiments, the linear motion may be augmented by changing the direction of the linear motion. For example, a pivot could be installed at the bottom of the guide rods, and a gear attached to the linear motion driver such that the linear motion causes the guide rods to tilt, changing the direction of the linear motion during each travel along the guide rods. Alternatively, a separate motor, driver, or actuator could be installed, which changes the pivot angle of the guide rods independently of the linear motion.

Optionally, the device may include a number of other functions to enhance the user experience. For example, a grippable surface may be molded to the outside of the housing to provide better grip in the hand. The device may contain the ability to warm the sheath to an optimal temperature prior to and during use. The device may also contain additional methods of stimulation in addition to the primary linear motion, such as suction, vibration, or direct electrical stimulation. The device may be made more portable by designing it to operate from batteries contained within the device housing. It will be apparent to one skilled in the art, that the linear motion could be generated by some other means than a rotary electric motor.

Figure 2:
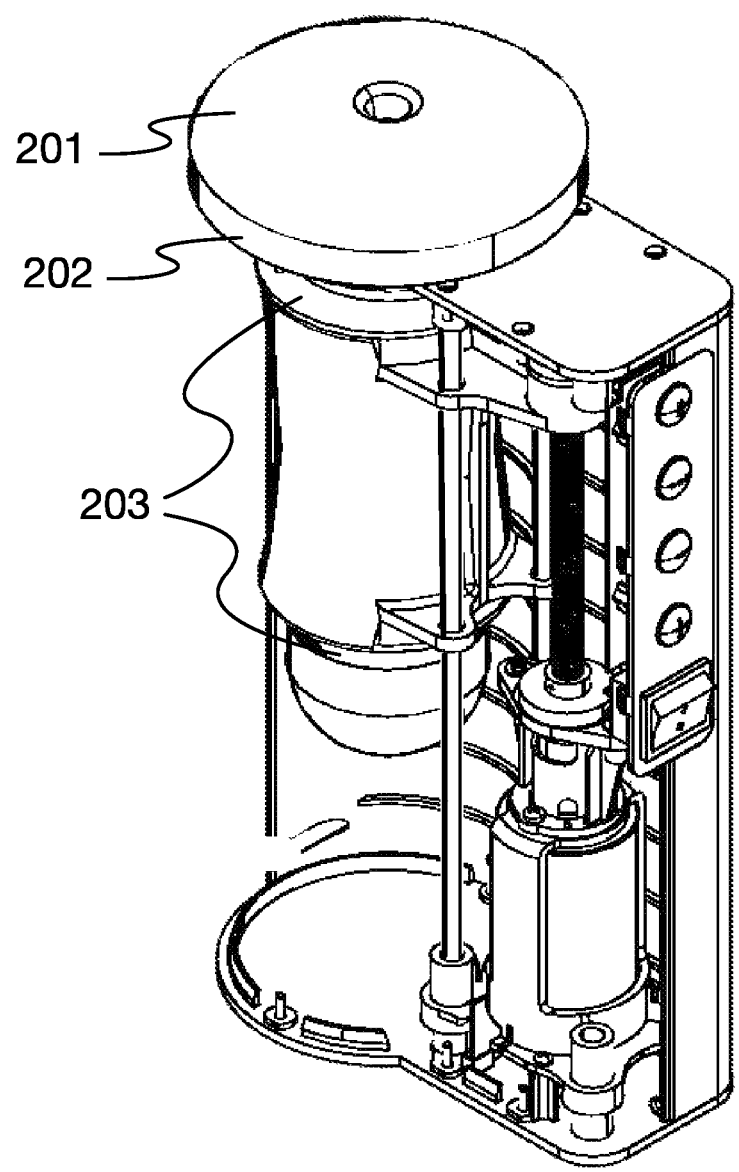
FIG. 2 shows additional components of the internal workings of an exemplary male sexual stimulation device as set forth in a preferred embodiment.

FIG. 1 shows the internal workings of an exemplary male sexual stimulation device 100 according to a preferred embodiment. In this embodiment, the device is a small handheld unit powered by a low voltage, external direct current (DC) power source. Inside the device is a framework 101 to which the mechanical parts of the device are attached. Attached to the framework 101 is a small DC motor 102 with a motor shaft 103, which drives the stimulation mechanism. A screw shaft 104 is affixed to the motor shaft 103 of the DC motor 102, such that the screw shaft 104 rotates as the motor shaft 103 of the DC motor 102 rotates. The polarity of voltage to the DC motor 102 may be reversed so that the motor shaft 103 of the DC motor 102 rotates both clockwise and counter-clockwise. A flex coupling 105 between the motor shaft 103 of the DC motor 102 and screw shaft 104 compensates for any misalignment between the two during operation. A nut 106 is placed around the screw shaft 104 and attached to a bracket 107, which is held in a particular orientation by guide rods 108, such that the nut 106 and bracket 107 travel in a linear motion as the screw shaft 104 is turned. Affixed to the bracket 107 is a gripper 109, which travels in a linear motion along with the bracket 107. A hole 110 in the framework 101, allows for the insertion of a flexible sleeve as shown in FIG. 2. Magnetic sensors 111 may be used to set limits of operation of the nut 106, or to ensure that the nut 106 is at one end of its range of motion before starting operation of the device. An integrated circuit (not visible in drawing) 112 may be used to control the operation of the device.

FIG. 2 shows additional components of the internal workings of an exemplary male sexual stimulation device 200 as set forth in a preferred embodiment. A flexible sleeve 201 made of either thermoplastic elastomer (TPE) or thermoplastic rubber (TPR) or silicone is inserted through a hole 110 in the framework 101 and through gripper 109. Sleeve 201 is prevented from accidentally slipping into device 200 by a ridge 202 at the open end of sleeve 201, and is held in the proper position by ridges 203 on the sleeve 201 at both ends of gripper 109. During operation, gripper 109 slides in a reciprocal linear motion 201 providing pressure and motion against the penis inside the sleeve 201 in a manner similar to sexual intercourse or manual masturbation. Depending on the configuration, gripper 109 may either grip sleeve 201 and move sleeve 201 along the penis, or it may slide along the outside of sleeve 201, not moving the sleeve relative to the penis. Also depending on configuration, gripper 109 may be made of rigid, semi-rigid, or compliant materials, and other shapes might be used (e.g., partial tube, ring, half-ring, multiple rings, loops of wire) and may contain rollers or bearings to increase stimulation and reduce friction against the flexible sleeve 201.

Figure 3:
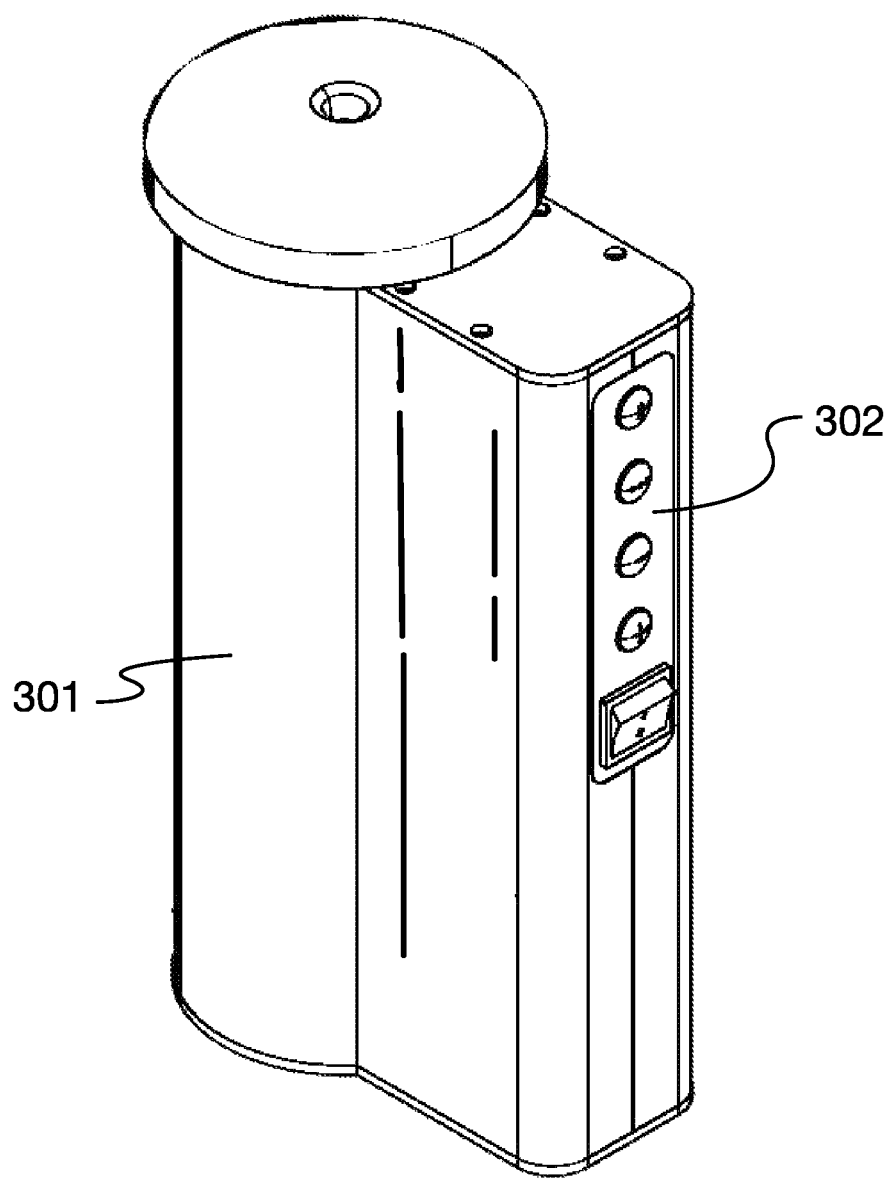
FIG. 3 shows the external structure of an exemplary male sexual stimulation device.

FIG. 3 shows the external structure 300 of an exemplary male sexual stimulation device. The housing 301 of the device is made of plastic, and is attached to the framework in such a way as to provide additional support and structure to the device. User controls 302 in the form of buttons and switches and their associated electronics are built into the housing. The housing has an opening at one end corresponding to the opening 110 in the framework 101, into which the flexible sleeve 201 is inserted. The penis is inserted into the sleeve 201 at the end of the device, and is stimulated by the reciprocal linear motion of the gripper 109 inside the device. The user controls the speed, pattern, and location of stimulation using the controls 302 on the outside of the housing 301.

Figure 4:
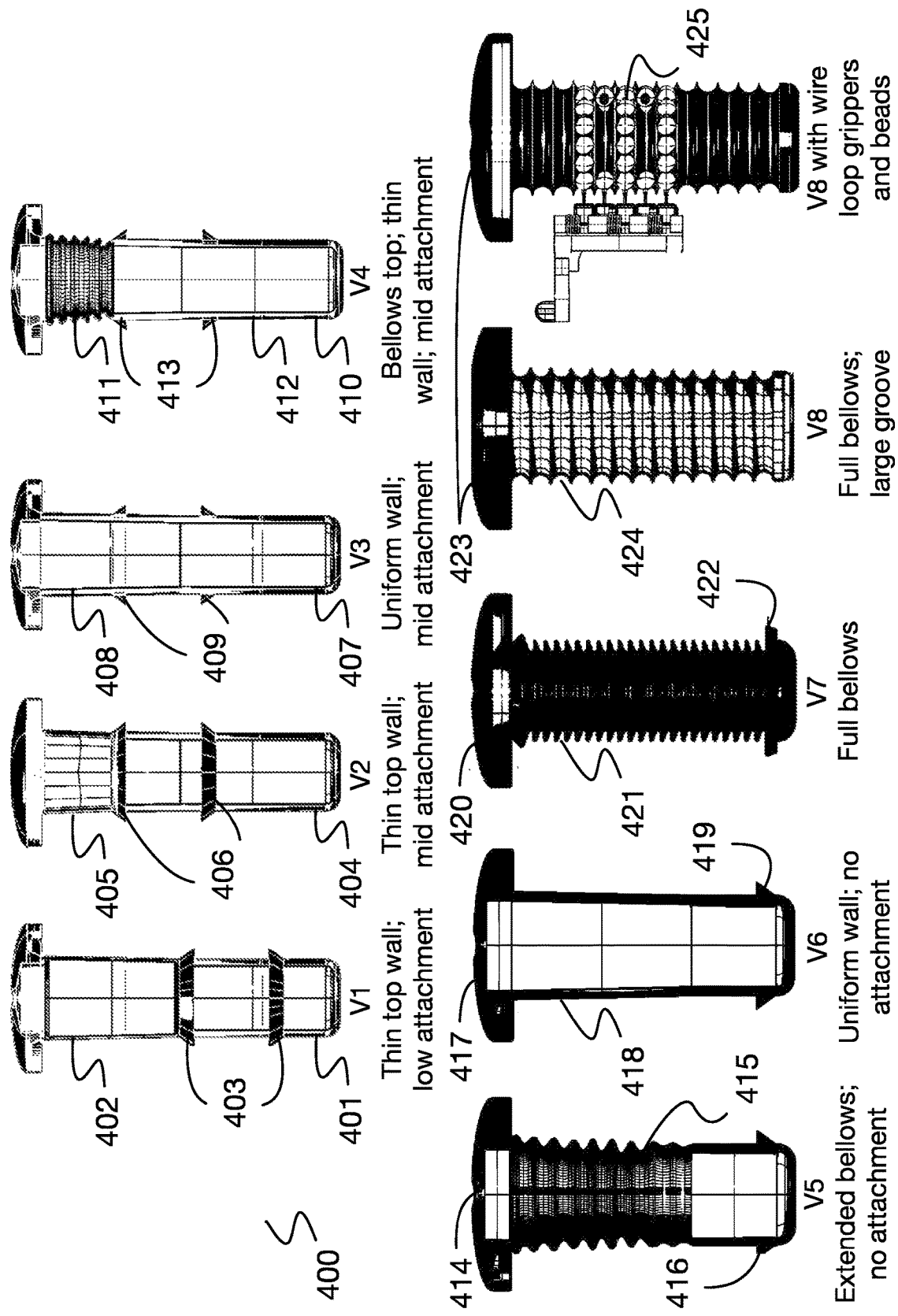
FIG. 4 shows exemplary variations of the sleeve and gripper aspects of an exemplary male sexual stimulation device.

FIG. 4 shows exemplary variations 400 of the sleeve 201 and gripper 109 aspects of an exemplary male sexual stimulation device. As noted above, different configurations of the sleeve 201 and gripper 109 are possible to allow optimal fit and sensation for penises of different lengths and girths, and to allow the user a choice of pressure, gripper location, and sensation. Sleeve variant one 401 has a thin top wall 402 with a low point of attachment 403 to the gripper 109. Sleeve variant two 404 has a thin top wall 405 with a middle point of attachment 406 to the gripper 109. Sleeve variant three 407 has a uniform wall thickness 408 with a middle point of attachment 409 to the gripper 109. Sleeve variant four 410 has a bellows top 411, a thin wall 412, and a middle point of attachment 413. Sleeve variant five 414 has an extended bellows 415 and no attachment to the gripper 109 other than a stopper at the end 416, allowing the gripper 109 to slide along the outside of the sleeve 414. Sleeve variant six 417 has a uniform wall thickness 418 and no attachment to the gripper 109 other than a stopper at the end 419, allowing the gripper 109 to slide along the outside of the sleeve 417. Sleeve variant seven 420 has a full bellows design 421 and no attachment to the gripper 109 other than a stopper at the end 422, allowing the gripper 109 to slide along the outside of the sleeve 420. Sleeve variant eight 423 has a full bellows design with large grooves 424 into which fits a gripper made of wire loops with beads attached 425.

Figure 5:
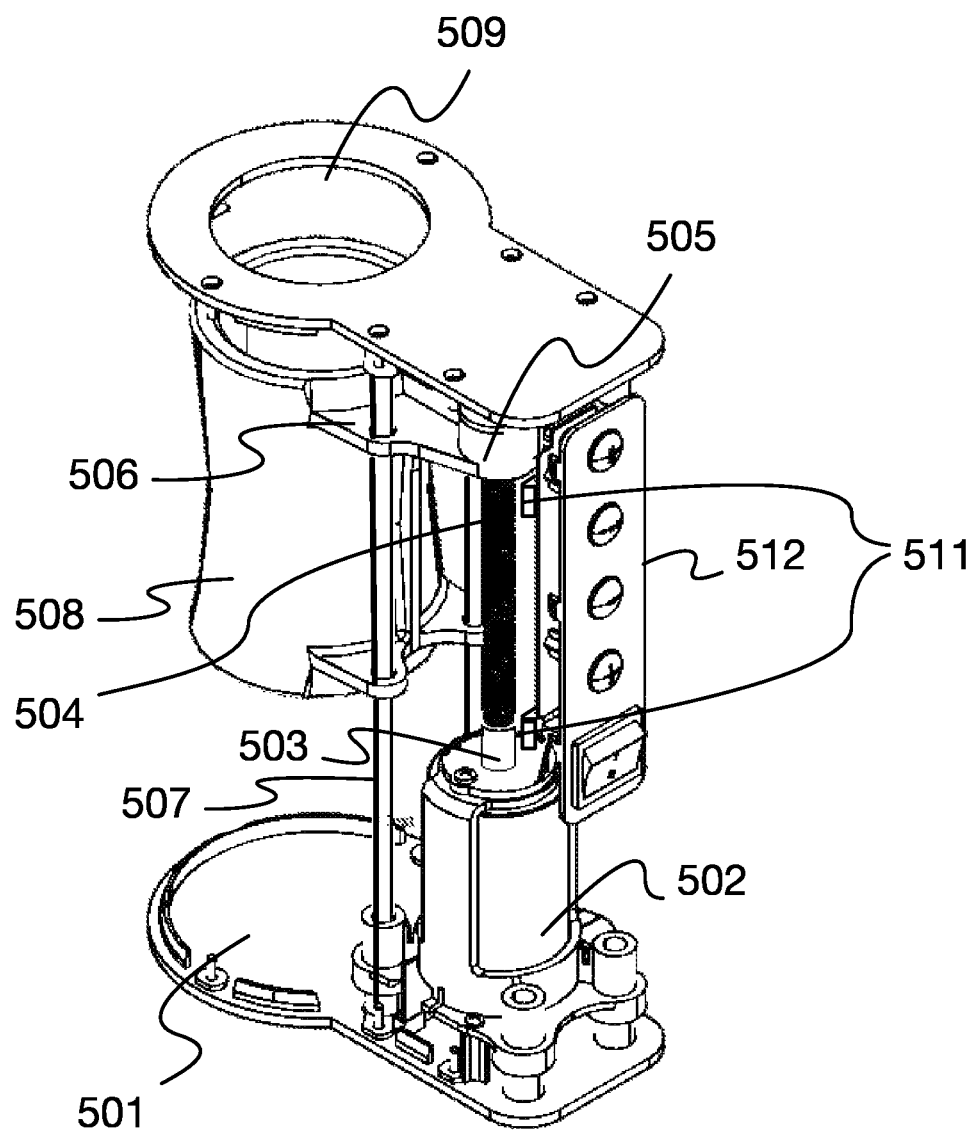
FIG. 5 shows the internal workings of an exemplary male sexual stimulation device according to another preferred embodiment.

FIG. 5 shows the internal workings of an exemplary male sexual stimulation device 500 according to another preferred embodiment. In this embodiment, the device is a small handheld unit powered by a low voltage, external direct current (DC) power source. Inside the device is a framework 501 to which the mechanical parts of the device are attached. Attached to the framework 501 is a small DC motor 502 with a motor shaft 503, which drives the stimulation mechanism. A screw shaft 504 is affixed directly to the motor shaft 503 of the DC motor 502, such that the screw shaft 504 rotates as the motor shaft 503 of the DC motor 502 rotates. The polarity of voltage to the DC motor 502 may be reversed so that the motor shaft 503 of the DC motor 502 rotates both clockwise and counter-clockwise. In this embodiment, the flex coupling 105 has been eliminated, allowing the device to be constructed in a more compact form, approximately 2 cm shorter in overall length. A nut 505 is placed around the screw shaft 504 and attached to a bracket 506, which is held in a particular orientation by guide rods 507, such that the nut 505 and bracket 506 travel in a linear motion as the screw shaft 504 is turned. Affixed to the bracket 506 is a gripper 508, which travels in a linear motion along with the bracket 506. A hole 509 in the framework 501, allows for the insertion of a flexible sleeve 201 as previously shown in FIG. 2. Magnetic sensors 511 may be used to set limits of operation of the nut 506, or to ensure that the nut 506 is at one end of its range of motion before starting operation of the device. An integrated circuit (not visible in drawing) 512 may be used to control the operation of the device.

Figure 6:
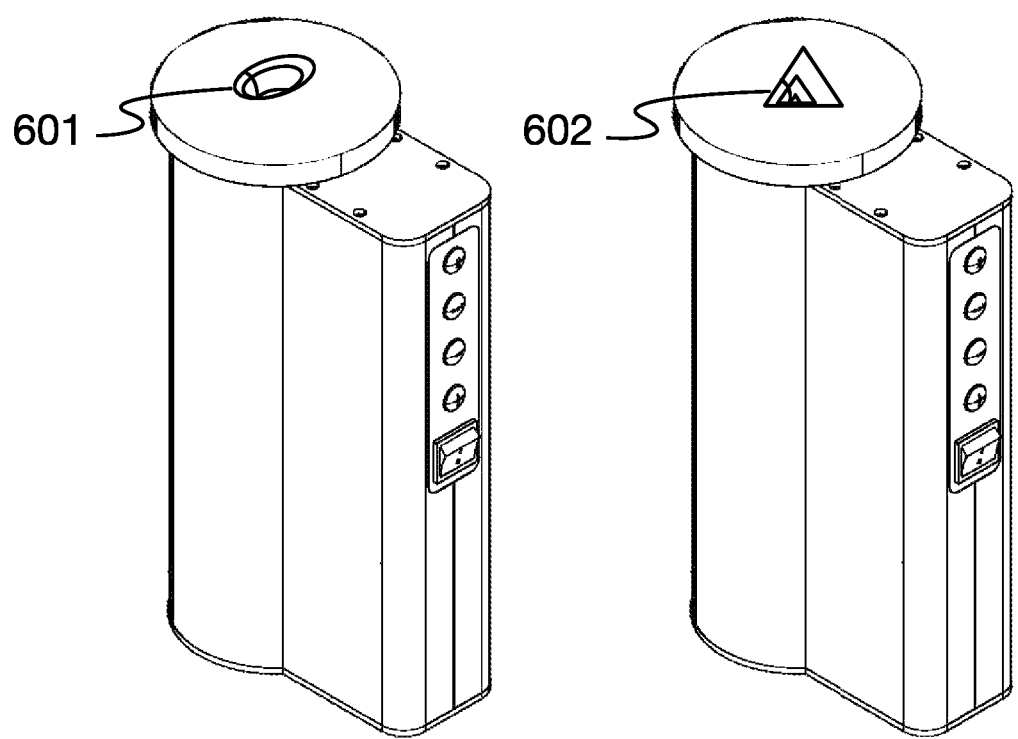
FIG. 6 shows additional exemplary variations of the sleeve aspect of an exemplary male sexual stimulation device.

FIG. 6 shows additional exemplary variations 600 of the sleeve aspect of an exemplary male sexual stimulation device. In this embodiment, the opening in the sleeve may be other than circular. For example, the opening may be elliptical in shape 601 or triangular in shape 602.

Figure 7:
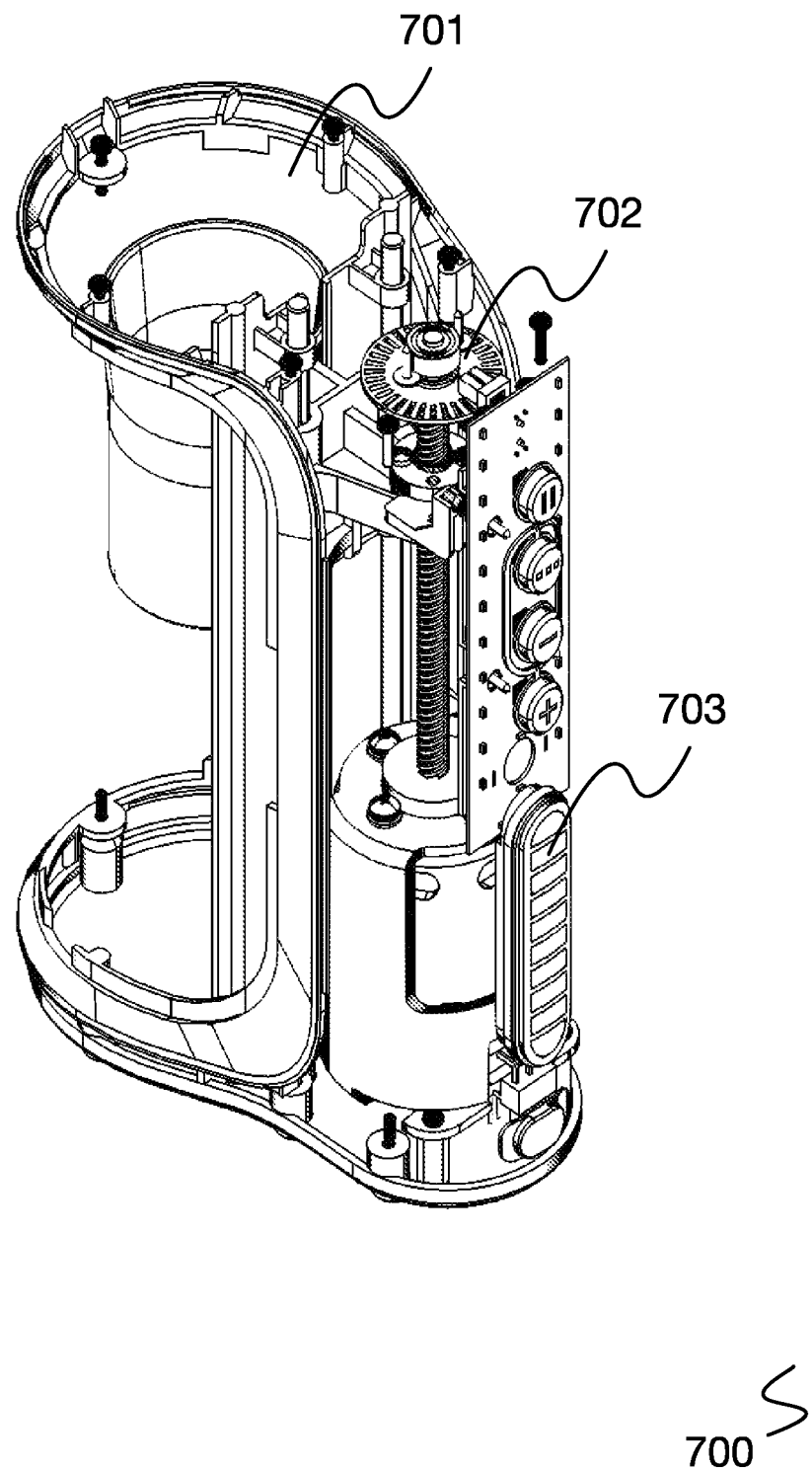
FIG. 7 shows an aspect of an embodiment of male sexual stimulation device according to another preferred embodiment.

FIG. 7 shows an aspect of an embodiment of male sexual stimulation device according to another preferred embodiment 700. In this embodiment, the framework 701 is made from a molded plastic structure. An optical rotary encoder 702 is used to determine the rotational speed and number of rotations of the screw shaft to control patterns of stimulation. A series of light emitting diodes (LEDs) 703 are used to indicate the mode of operation of the device.

Figure 8:
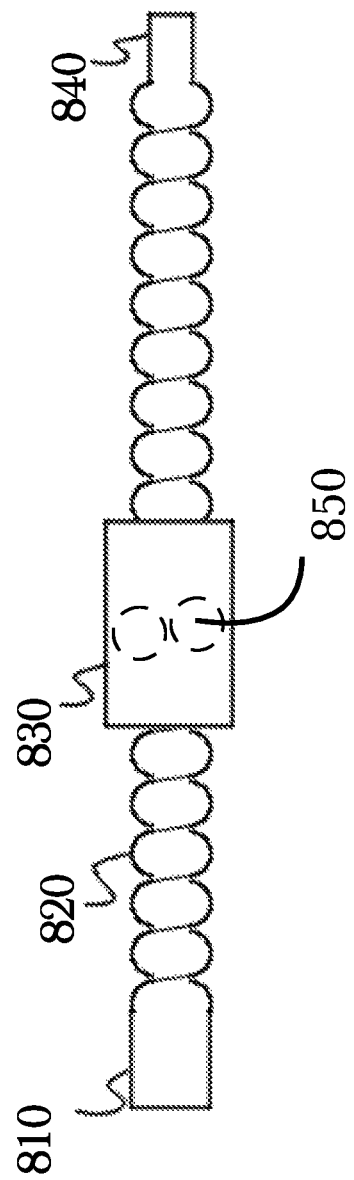
FIG. 8 shows an aspect of an embodiment of male sexual stimulation device comprising a ball screw mechanism.

FIG. 8 shows an aspect of an embodiment of male sexual stimulation device comprising a ball screw mechanism. A ball screw mechanism may be used to translate rotational motion to linear motion and comprises a threaded shaft 820 with two ends 810, 840, a ball assembly 830 containing a plurality of ball bearings 850 set at an angle equal to the angle of the threads on the shaft, which allow a rotation along a threaded body 820 to translate into linear motion. A ball screw mechanism may be used as a linear motion driver. Ball screws are useful because they can withstand large thrust loads with minimum internal friction. Variations on this mechanism include the threadless ballscrew (also known as a rolling ring drive) wherein the shaft is threadless, and a series of bearings are set at an angle in a housing around the shaft, the angle determining the rate of linear motion per revolution of the rod.

Figure 9:
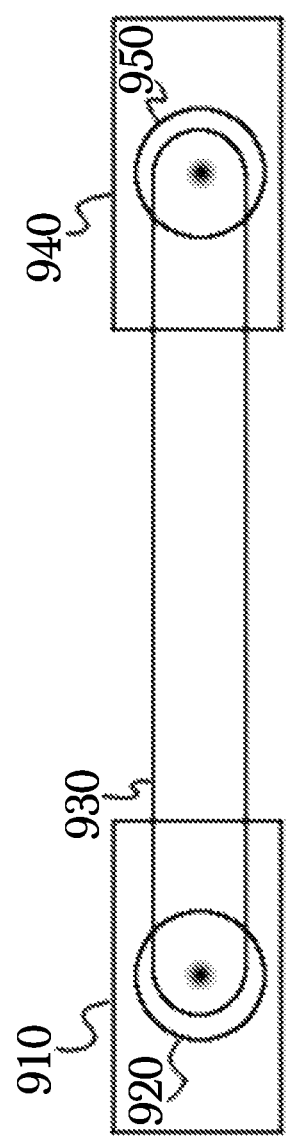
FIG. 9 shows an aspect of an embodiment of male sexual stimulation device comprising a belt-drive linear actuator.

FIG. 9 shows an aspect of an embodiment of male sexual stimulation device comprising a belt-drive linear actuator. A belt-drive linear actuator may be used to produce linear motion through the use of two spinning wheel-like devices 920, 950 built into housing with motors 910, 940 to spin, causing linear motion of a belt wrapped around both wheels 930, allowing for linear motion in two directions, depending on the examined side of the belt, and depending further on the direction in which the wheels 920, 950 are spinning. In this way, a belt-driven linear actuator may be an alternative method for moving a gripper 109 up or down. Some belt-drive linear actuators have a single motor at one end and a free-spinning pulley at the other end, instead of motors at both ends.

Figure 10:
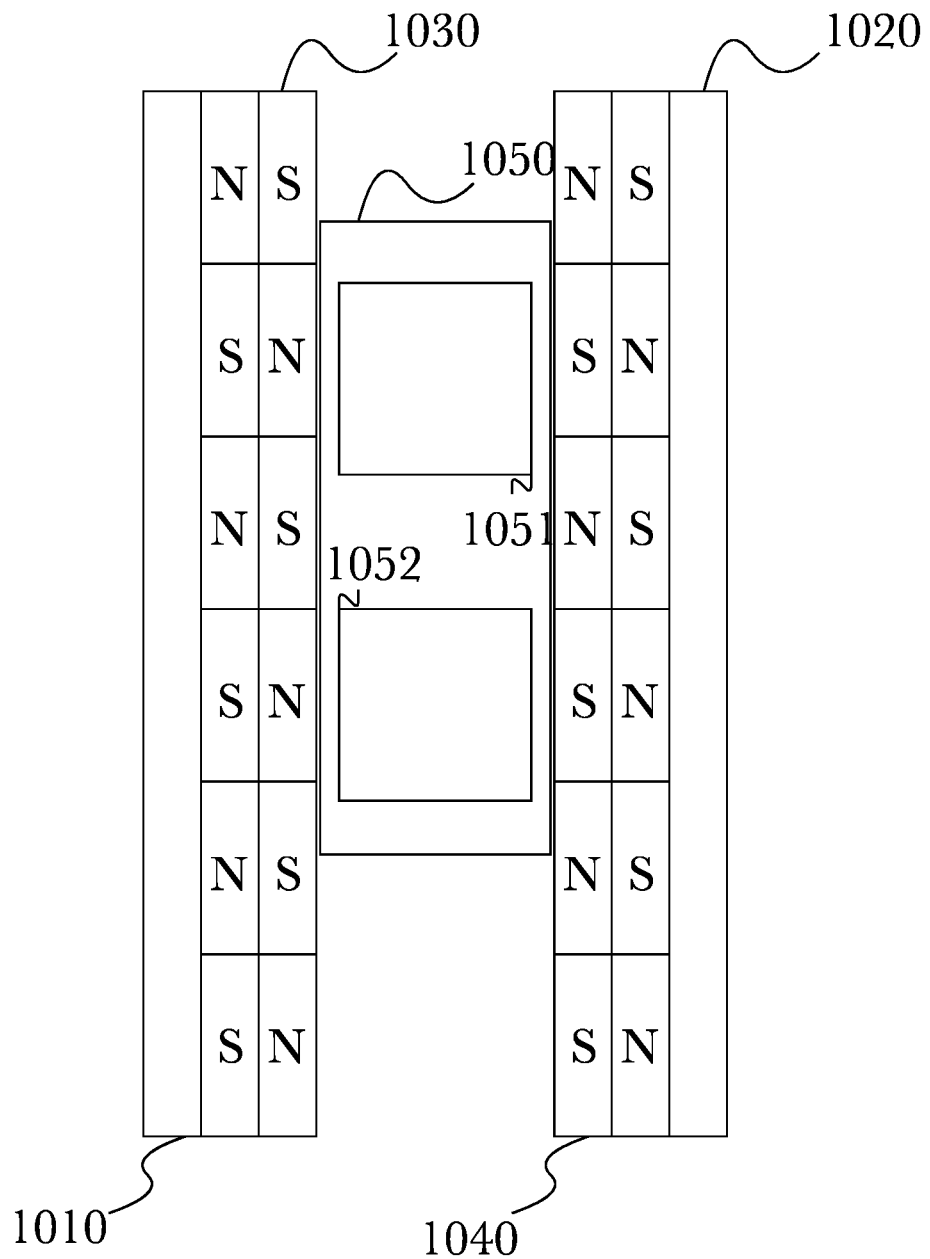
FIG. 10 shows an aspect of an embodiment of male sexual stimulation device comprising linear motor.

FIG. 10 shows an aspect of an embodiment of male sexual stimulation device comprising linear motor. A linear motor has a similar electromagnetic operation to a traditional DC motor, but with the stator 1010-1040 and rotor 1050 being "unrolled," such that linear force is produced instead of rotational force (torque). Shown in this figure is a U-channel synchronous linear motor, with a stator comprising arrays or planes of magnetic pairs 1030, 1040, resting on a substrate 1010, 1020, with a rotor 1050 comprising two coils (wound in parallel to the stators) 1051, 1052 which are mechanically connected, and operate similarly to the coils in a regular motor in that current flowing into the coils (typically through electrical contacts called brushes) allows mechanical motion to be achieved in either direction along the plane of magnets 1030, 1040. Variations of linear motors include alternating-current linear induction motors (LIM) and linear synchronous motors (LSM).

Figure 11:
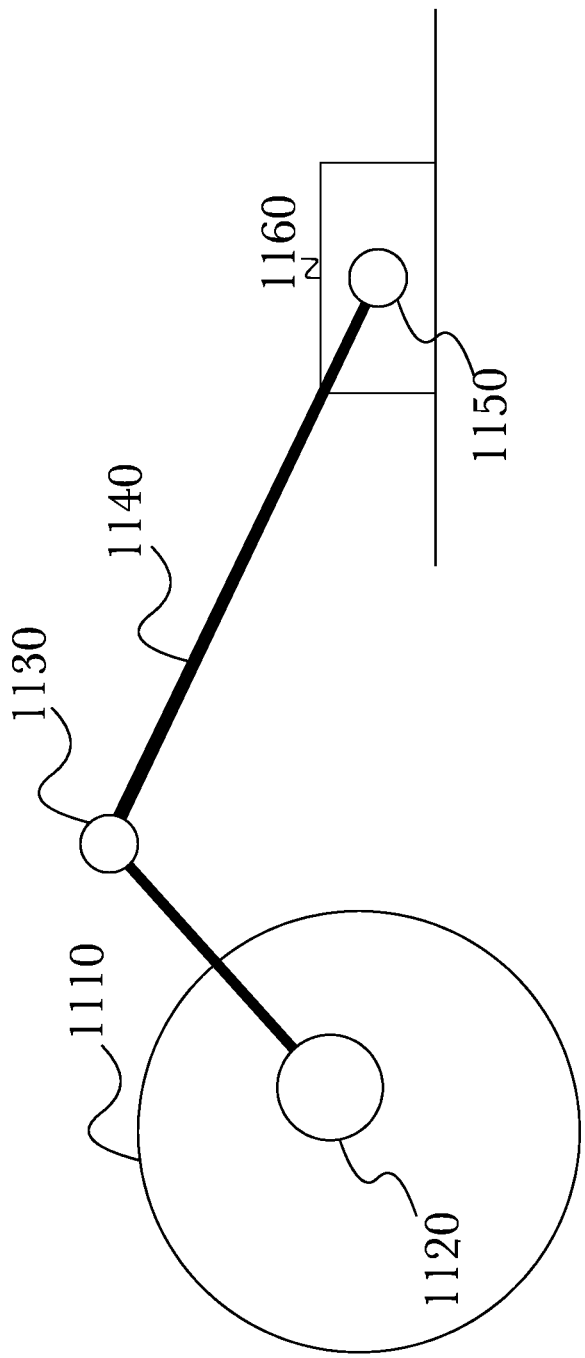
FIG. 11 shows an aspect of an embodiment of male sexual stimulation device comprising slider-crank mechanism.

FIG. 11 shows an aspect of an embodiment of male sexual stimulation device comprising a slider-crank mechanism. An alternative method for linear motion of a gripper or any other component in a male sexual stimulation device may be a slider-crank mechanism, comprising a wheel 1110 which may itself be powered by a built-in motor or by some other motor in a system, a bar-like arm 1140, a connecting wheel 1120 which is smaller than a first wheel 1110, a joint 1130 allowing for the arm 1140 to bend around the joint, an object to push or pull 1160, and a connecting wheel-like joint to the object 1150. As a wheel 1110 is turned, the arm 1140 may be retracted or pushed while still being connected to a wheel-like joint 1120, resulting in force being applied to an object 1160 attached by a joint 1150 to an arm 1140.

Figure 12:
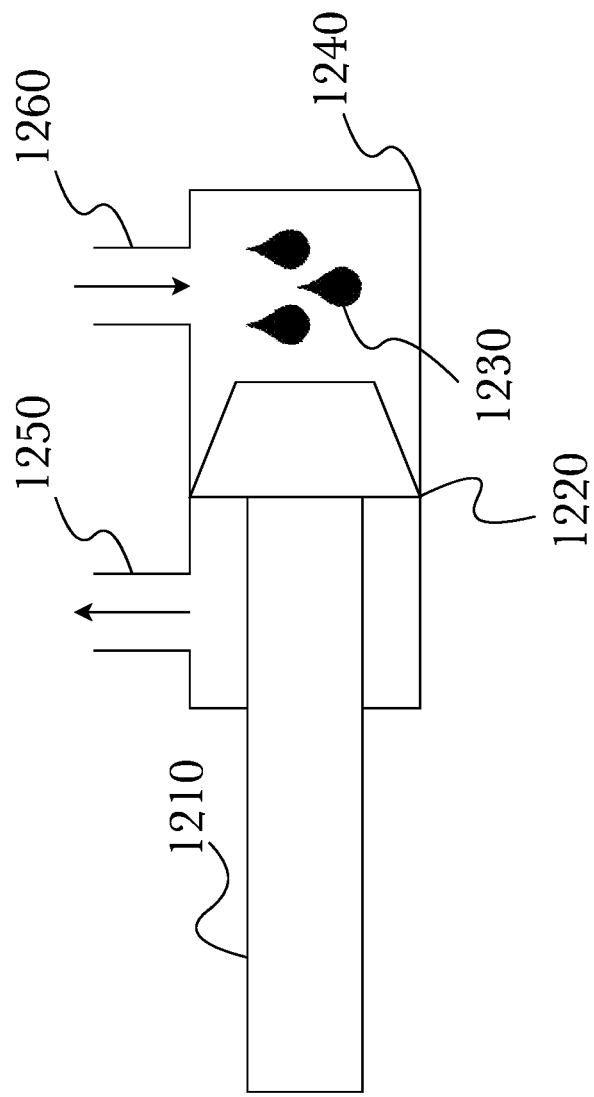
FIG. 12 shows an aspect of an embodiment of male sexual stimulation device comprising hydraulic or pneumatic linear actuator.

FIG. 12 shows an aspect of an embodiment of male sexual stimulation device comprising a hydraulic or pneumatic linear actuator. A piston 1210 exists as part of a pneumatic or hydraulic linear actuator, with a piston head and gasket 1220, actuator body 1240, a retract flow port 1250, extend flow port 1260, and a fluid chamber capable of holding either air, hydraulic fluid, or some other appropriate liquid or gas 1230. By fluid flowing through the extend flow port 1260 into the fluid chamber 1230, pressure is exerted on a piston head and gasket 1220, causing the piston bar 1210 to extend outward as the fluid chamber 1230 fills with fluid. A retraction of the piston bar 1210 may be accomplished by fluid flowing from the retract flow port 1250 into the fluid chamber 1230, causing pressure to build on the opposite side of the piston and gasket 1220, allowing for bi-directional linear motion from such an actuator.

Figure 13:
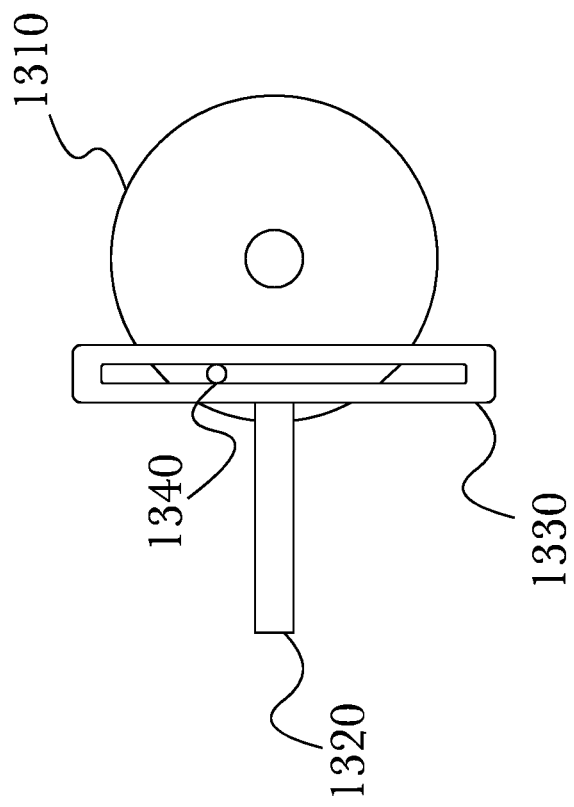
FIG. 13 shows an aspect of an embodiment of male sexual stimulation device comprising a scotch yoke mechanism.

FIG. 13 shows an aspect of an embodiment of male sexual stimulation device comprising a scotch yoke mechanism. A large wheel-like object 1310 holds a yoke 1330 by a connecting object 1340, with a yoke 1330 having a piston 1320 connected, allowing the rotation of the large wheel-like object 1310 to push or pull the yoke 1330 and therefore translate rotational motion into linear motion of a piston 1320.

Figure 14:
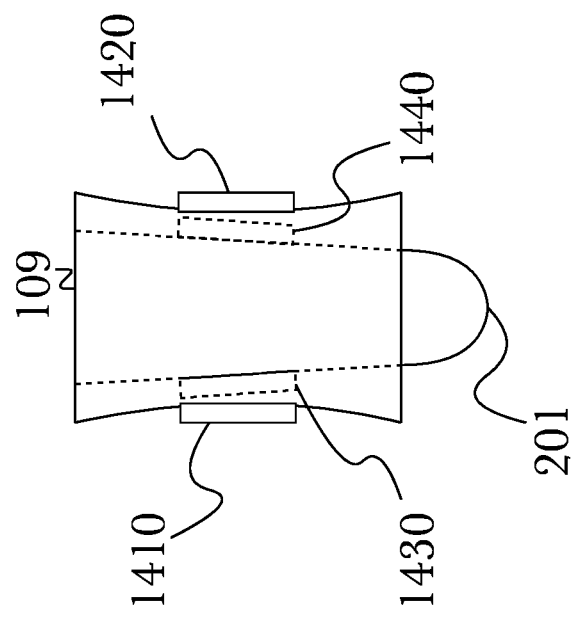
FIG. 14 shows an aspect of an embodiment of male sexual stimulation device comprising a magnetic gripper.

FIG. 14 shows an aspect of an embodiment of male sexual stimulation device comprising a magnetic gripper. According to this aspect, the flexible sleeve 201 is affixed to the gripper by magnets 1410, 1420 which may pair with magnets 1430, 1440 attached to the exterior of an insertable sleeve 201, rather than affixing the sleeve to the gripper mechanically.

Figure 15:
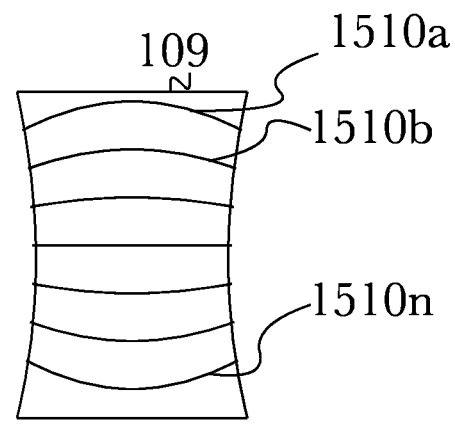
FIG. 15 shows an aspect of an embodiment of male sexual stimulation device comprising a gripper with built-in heating elements.

FIG. 15 shows an aspect of an embodiment of male sexual stimulation device comprising a gripper with built-in heating elements. Heating elements are shown 1510a-n, being affixed to a gripper 109, such heating elements allowing a gripper 109 to be warmed to a preset temperature allowing for the sexual stimulation device to be self-heating and thereby more comfortable to users.

Figure 16:
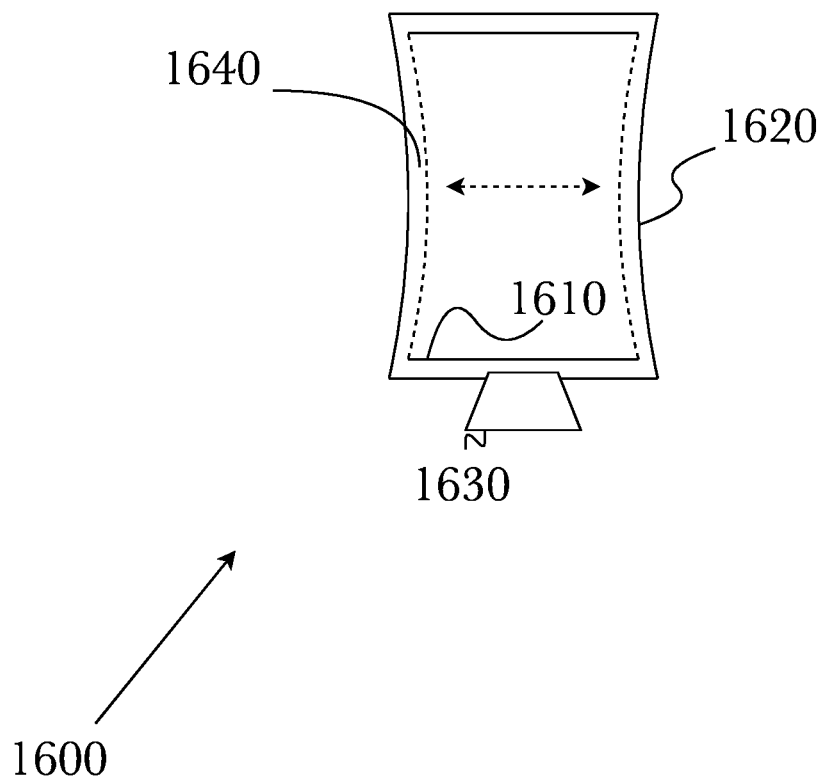
FIG. 16 shows an aspect of an embodiment of male sexual stimulation device comprising an inflatable gripper.

FIG. 16 shows an aspect of an embodiment of male sexual stimulation device comprising an inflatable gripper 1600. According to this aspect, a gripper 1600 is now presented as a volumetric object with a cavity 1640 between an exterior and interior wall 1610, 1620, capable of being filled with either air or some other fluid from a valve 1630, which causes at least a portion of the gripper to expand, allowing adjustment of the size or tightness of the gripper, and allowing a difference in texture and feel versus a rigid gripper. The pressure of a fluid between the walls 1610, 1620 may be adjustable or may be pre-set on item fabrication. A person of ordinary skill in the art will recognize that the inflatable gripper 1600 and cavity 1600 may be of any shape or size, and may be made from any suitable flexible material or (as shown here) a combination of rigid and flexible materials.

Figure 17:
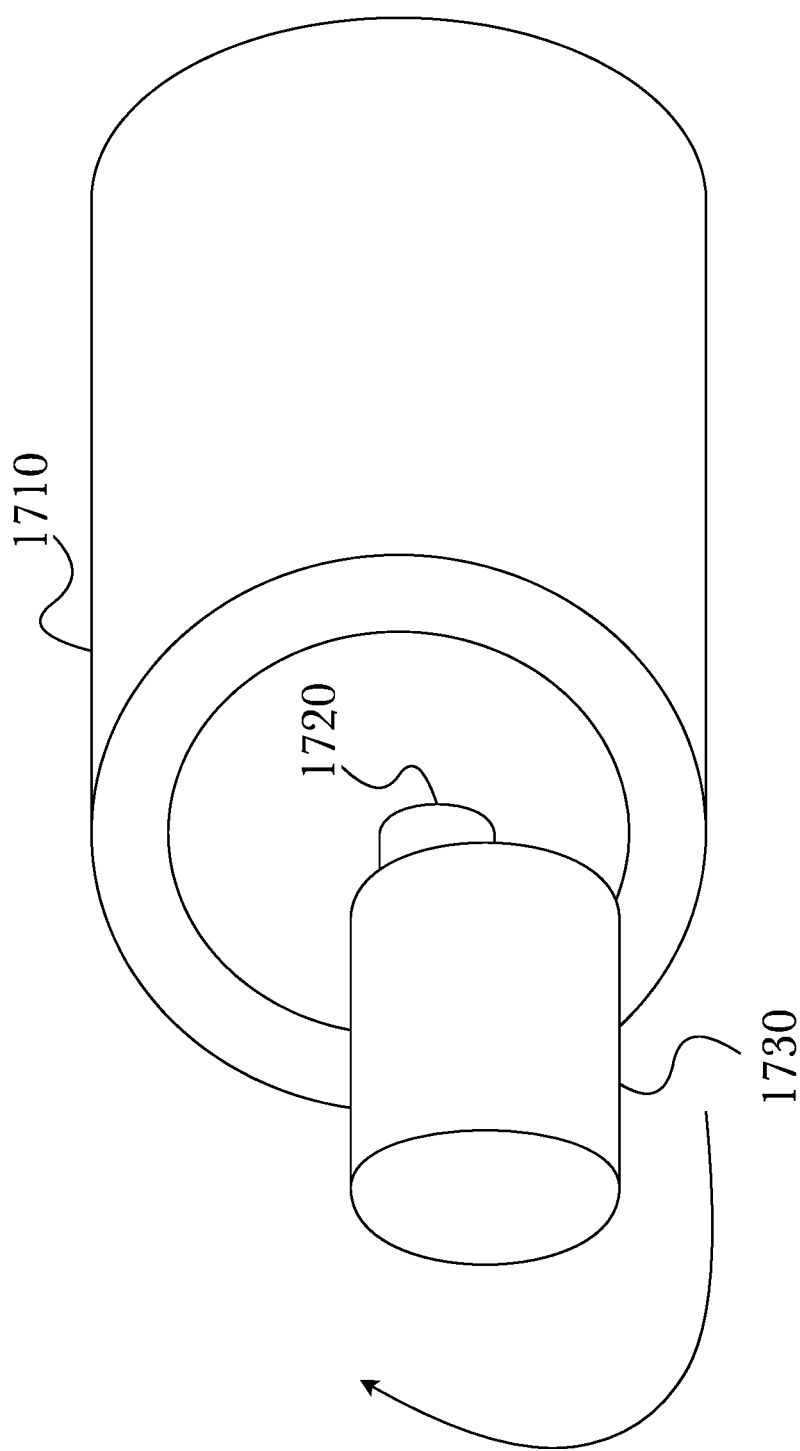
FIG. 17 shows an aspect of an embodiment of male sexual stimulation device comprising a vibrating gripper.

FIG. 17 shows an aspect of an embodiment of male sexual stimulation device comprising a vibrating motor. An exemplary motor 1710 is shown, with an unevenly distributed weight 1730 attached to an externally rotating element 1720, which, when the motor 1710 is activated, rotates generating force due to the unevenness of the weight 1730, allowing for the mechanism to vibrate. A vibrating motor as shown may be used to cause the gripper to vibrate, providing additional stimulation.

Figure 18:
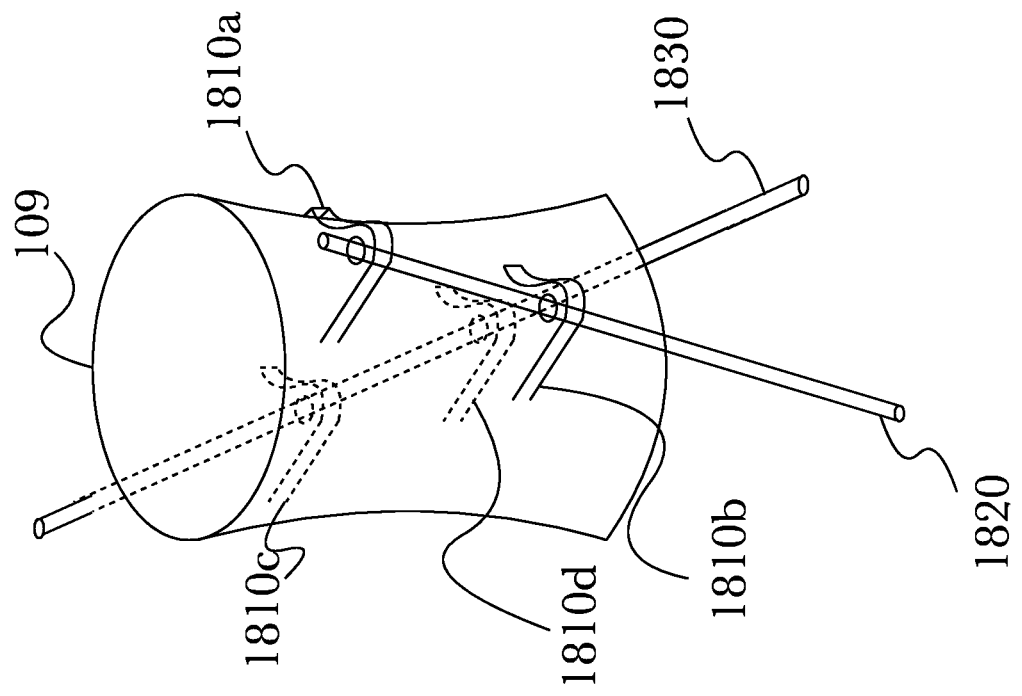
FIG. 18 shows an aspect of an embodiment of a male sexual stimulation device in which rotational motion is used in addition to linear motion.

FIG. 18 shows an aspect of an embodiment of a male sexual stimulation device in which rotational motion is used in addition to linear motion. Shown are four brackets 1810a-d, offset from one another and not aligning vertically, such that the gripper is held vertically when inserted onto guide rods 1820, 1830. The guide rods may be configured to be tilted, such that when the gripper 109 is moved up and down on the guide rods 1820, 1830, the gripper 109 partially rotates, providing rotational motion as well as linear motion. Alternate configurations would include guide rods 1820, 1830 formed in a spiral, with brackets 1810a-d on the gripper 109 vertically aligned, such that when the gripper 109 is moved up and down on the guide rods 1820, 1830, the gripper 109 partially rotates, providing rotational motion as well as linear motion.

Figure 19:
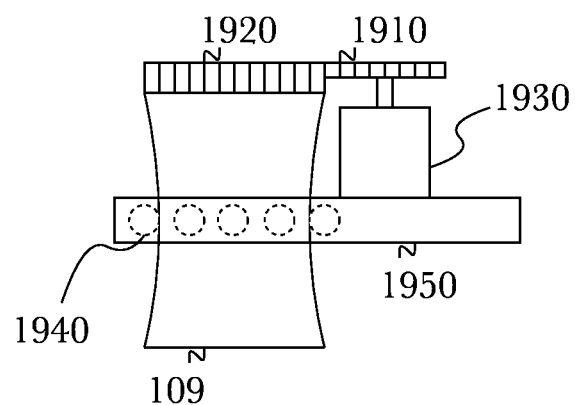
FIG. 19 shows an aspect of another embodiment of a male sexual stimulation device in which rotational motion is used in addition to linear motion.

FIG. 19 shows an aspect of another embodiment of a male sexual stimulation device in which rotational motion is used in addition to linear motion. A motor 1930 is shown, connected to a small gear train comprising two gears 1910, 1920, and providing rotational motion to a gripper 109. A bracket 1950 may hold the gripper 109 in a ball bearing mechanism containing ball bearings 1940 which allows the gripper 109 to rotate under power of the motor 1930 independently of the linear motion of the bracket parallel to the longitudinal axis of the gripper 109. A person of ordinary skill in the art will recognize that any rotational bearing mechanism (e.g., a sleeve bearing) may be used.

Figure 20:
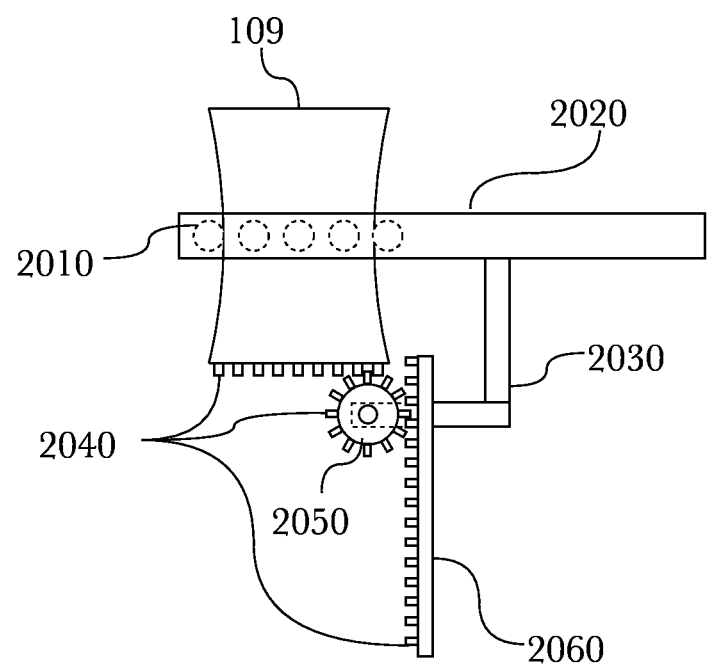
FIG. 20 shows an aspect of another embodiment of a male sexual stimulation device in which rotational motion is used in addition to linear motion.

FIG. 20 shows an aspect of another embodiment of a male sexual stimulation device in which rotational motion is used in addition to linear motion. Shown is a gripper 109, held by a bracket 2020 with a ball bearing mechanism containing ball bearings 2010. A small gear 2050 is also connected to the bracket by an arm 2030. The bottom edge of the gripper 109 contains teeth 2040 that engage with the teeth 2040 of the small gear. The teeth 2040 of the small gear simultaneously engage with the teeth 2040 of a linear rack 2060, which is mounted independently of the gripper/bracket/arm/gear mechanism. This configuration is commonly known as a "rack and pinion" mechanism wherein rotation of one part is translated through a gear into linear motion in another part, and vice-versa. When the bracket gripper/bracket/arm/gear mechanism is moved in a linear up and down motion, the small gear 2050 rotates because of its engagement with the linear rack 2060, causing the gripper 109 to rotate, correspondingly. In this example, the rotation of the gripper 109 is at a fixed rate to the linear motion. A person of ordinary skill in the art will recognize that any rotational bearing mechanism (e.g., a sleeve bearing) may be used.

Figure 21:
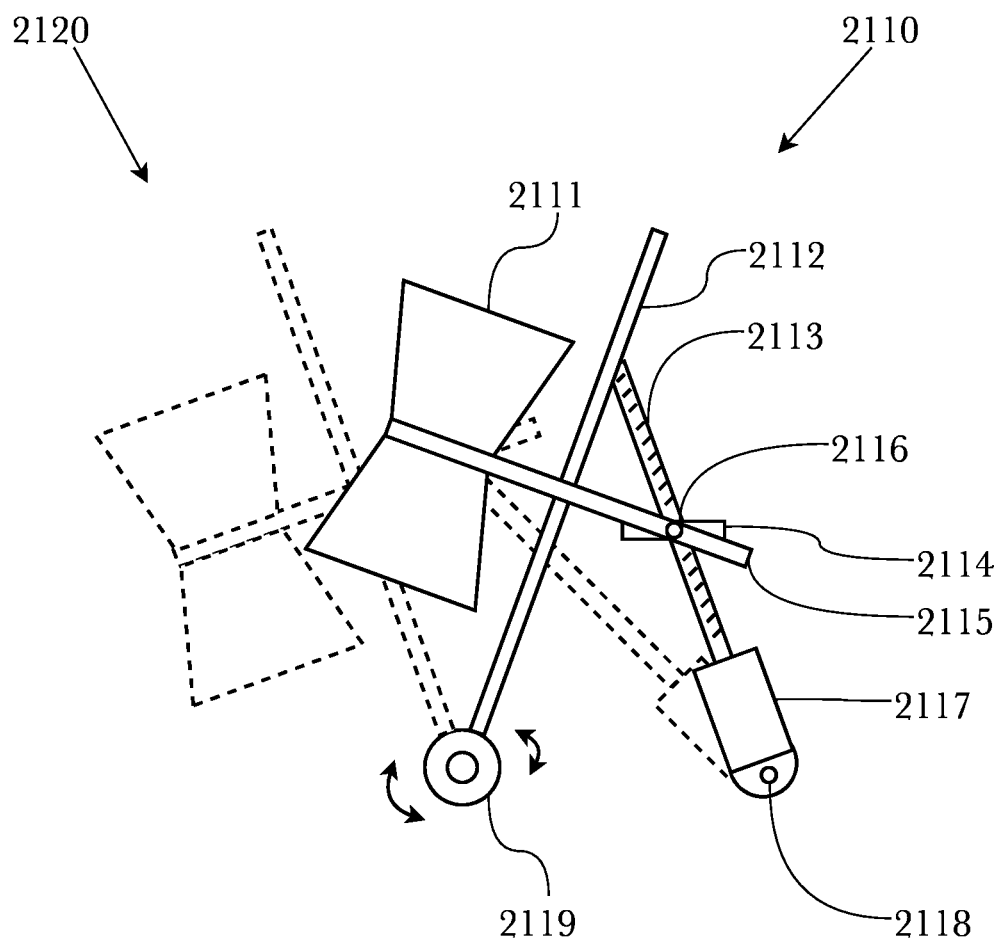
FIG. 21 shows an aspect of an embodiment of a male sexual stimulation device in which the axis of linear motion is movable.

FIG. 21 shows an aspect of an embodiment of a male sexual stimulation device in which the axis of linear motion is movable. The mechanism of this aspect comprises one or more guide rods 2112 which are connected to the device at the bottom using a first pivot 2119. A bracket 2115 is slid onto the guide rods 2112, and a gripper 2111 is attached to the bracket 2115. A motor 2117 is attached to the device with a second pivot 2118. A threaded screw 2113 is attached to the drive shaft of the motor 2117. The screw 2113 is threaded through a pivoting nut 2114, which pivoting nut 2114 is attached via a third pivot 2116 to the bracket 2115. When the motor 2117 is operated to retract the mechanism, the bracket 2114 is pulled down the guide rods and the guide rods/bracket/gripper mechanism is tilted toward the motor 2117, as shown in a first state 2110 of the mechanism. When the motor 2117 is operated to extend the mechanism, the bracket 2115 is pushed up the guide rods 2112 and the guide rods/bracket/gripper mechanism is tilted away from the motor 2117, as shown in a second state 2120 of the mechanism.

Figure 22:
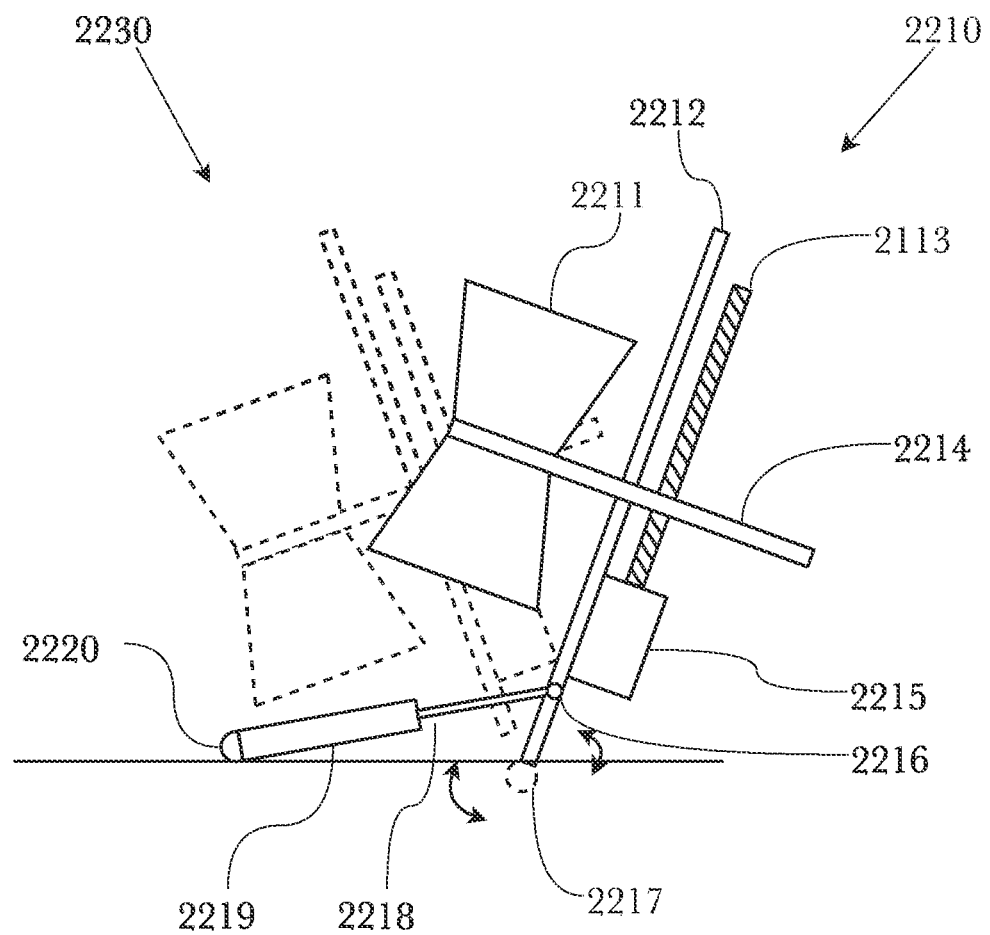
FIG. 22 shows an aspect of another embodiment of a male sexual stimulation device in which the axis of linear motion is movable.

FIG. 22 shows an aspect of another embodiment of a male sexual stimulation device in which the axis of linear motion is movable. The mechanism of this aspect comprises a gripper 2211 designed to grip a removable sleeve, one or more guide rods 2212 onto which the gripper 2211 is mounted, a screw 2213 threaded through a threaded portion of the bracket affixed to a shaft of a motor 2215, which may be utilized to move a gripper 2211 up or down through the use of a connected bracket 2214. There exists further, a first ball-joint 2217 allowing motion in at least two directions along an axis but potentially movement in movement in two axes for possible circular motion, connected to one or more actuators 2219 with an actuator piston 2218 which may be used to tilt the guide rods in one or more directions, independently of the linear motion of the bracket 2214 and gripper 2211. The actuators 2219 are connected to the device with a second ball-joint 2220, and the actuator pistons 2218 are connected to the guide rods 2212 with a pivot 2216. When an actuator 2119 is operated to extend the mechanism, the guide rods 2112 are tilted away from the actuator 2119, as shown in a first state 2210 of the mechanism. When an actuator 2119 is operated to retract the mechanism, the guide rods are tilted toward the actuator 2119, as shown in a second state 2230 of the mechanism.

Figure 23:
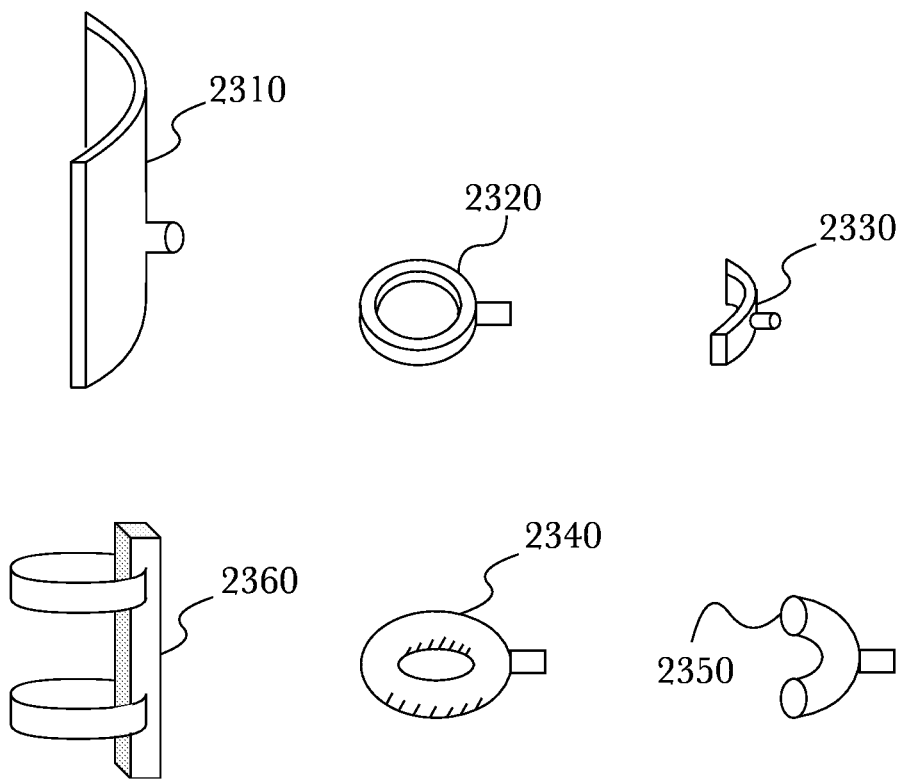
FIG. 23 shows exemplary variations of the gripper aspect of an exemplary male sexual stimulation device.

FIG. 23 shows exemplary variations of the gripper aspect of an exemplary male sexual stimulation device. Possible variations of a gripper may include a partial tube 2310, a ring 2320, a partial-ring 2330, wire or strap loops 2360, a rounded ring 2340, or partial rounded ring 2350. A person skilled in the art will recognize that other variations may be possible.

Figure 24:
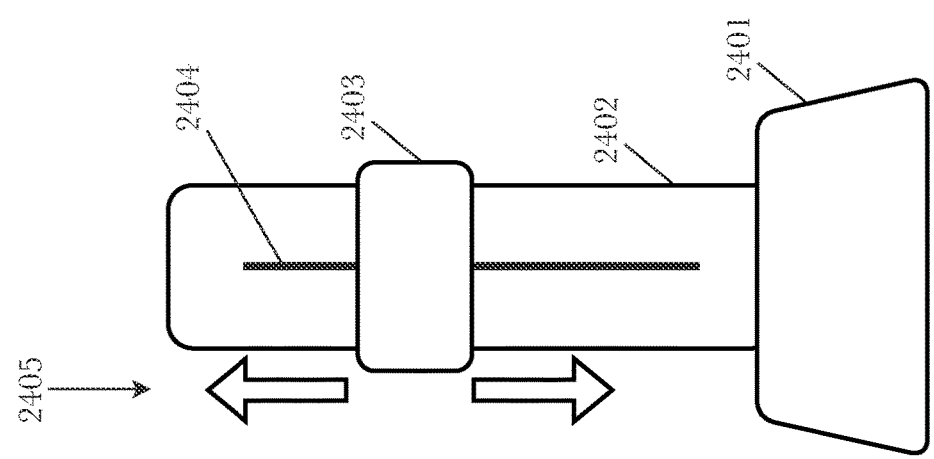
FIG. 24 shows an exemplary linear-movement motion sensing controller for sexual stimulation devices.

FIG. 24 shows an exemplary linear-movement motion sensing controller for sexual stimulation devices. In this embodiment, controller comprises a base 2401, a cylindrical shaft 2402, a slider ring 2403, and a slot 2404 for connecting slider ring 2403 to a sensor for detecting location of slider ring 2402 along length of shaft. This embodiment allows for control of sexual stimulation devices through a natural stroking movement by stroking slider ring 2403 up and down length of shaft 2405 with a hand.

Base 2401 allows for placement of controller on a stable surface such as a table, or for use as a handle or grip if controller is to be held in one hand and manipulated by or. Depending on configuration, base 2401 may be weighted for stability, or have means for attachment to stable surface such as suction cups, adhesives, or magnets.

Slider ring 2402 is placed around circumference of cylindrical shaft 2402 such that slider ring 2403 can be moved up and down shaft in a linear motion 2405. In this embodiment, slider ring 2403 is attached through a slot 2404 in shaft 2402 to a sensor for detecting location of slider ring 2403 along length of shaft. Any sensor or sensors capable of detecting location of slider ring 2403 along length of shaft may be used (a linear potentiometer would be one example of such a sensor). In or embodiments, slider ring 2403 may not be physically attached to shaft 2402, and a non-contact means of detecting location of slider ring 2403 may be used such as magnets within slider ring 2403, magnetic force of which is detected by magnetic sensors located inside shaft 2402. In some non-contact embodiments, it would be possible to for slider ring 2403 to be used to indicate not only linear motions up and down shaft 2405, but rotational movements about longitudinal axis of shaft, as well.

Shaft 2402 does not have to be cylindrical, and or cross-sectional shapes of shaft could be used (e.g., square, hexagonal, etc.).

Operation of the sexual stimulation device via the motion sensing controller can be done locally based on a wired or wireless connection between controller and device, or remotely based on connection between the controller and device through a local area network (LAN), wide area network (WAN), or via the Internet. Thus, the user of the controller and the user of the device may be the same person or different persons, and if different persons, may be co-located or remote from one another.

Figure 25:
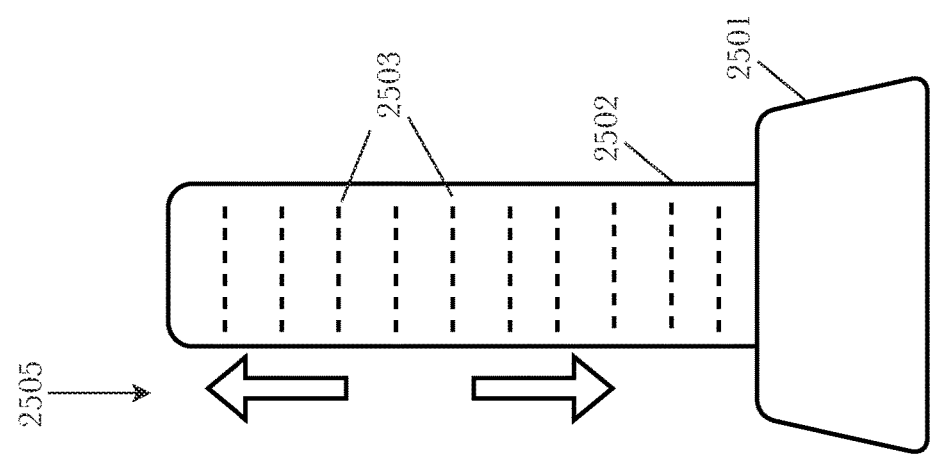
FIG. 25 shows another exemplary linear-movement motion sensing controller for sexual stimulation devices.

FIG. 25 shows another exemplary linear-movement motion sensing controller for sexual stimulation devices. In this embodiment, controller comprises a base 2501, a cylindrical shaft 2502, and a plurality of sensors along length of shaft 2503 configured to detect location of a hand or body part along length of shaft 2502. In this embodiment, shaft 2502 can be waterproofed, allowing for control of sexual stimulation devices either through a natural stroking movement by gripping shaft with a hand and stroking up and down length of shaft 2505 with hand, or by insertion of shaft into a bodily orifice such as a mouth or vagina. This allows for control of sexual devices through natural hand movements or intercourse-type movements via insertion into a bodily orifice.

Base 2501 allows for placement of controller on a stable surface such as a table, or for use as a handle or grip if controller is to be held in one hand and manipulated by or. Depending on configuration, base 2501 may be weighted for stability, or have means for attachment to stable surface such as suction cups, adhesives, or magnets.

Sensors along length of shaft 2503 are configured to detect movement of a hand or body part up and down shaft in a linear motion 2505. Any sensor or sensors capable of detecting location of a body part along length of shaft may be used. Examples of such sensors are pressure sensors, capacitive touch sensor, light detecting sensors, and ultrasonic sensors. Depending on placement and configuration of sensors, it may be possible to detect not only linear motions up and down shaft 2505, but rotational movements about longitudinal axis of shaft, as well. Note that shaft 2502 does not have to be cylindrical, and or cross-sectional shapes of shaft could be used (e.g., square, hexagonal, etc.).

Operation of the sexual stimulation device via the motion sensing controller can be done locally based on a wired or wireless connection between controller and device, or remotely based on connection between the controller and device through a local area network (LAN), wide area network (WAN), or via the Internet. Thus, the user of the controller and the user of the device may be the same person or different persons, and if different persons, may be co-located or remote from one another.

Figure 26:
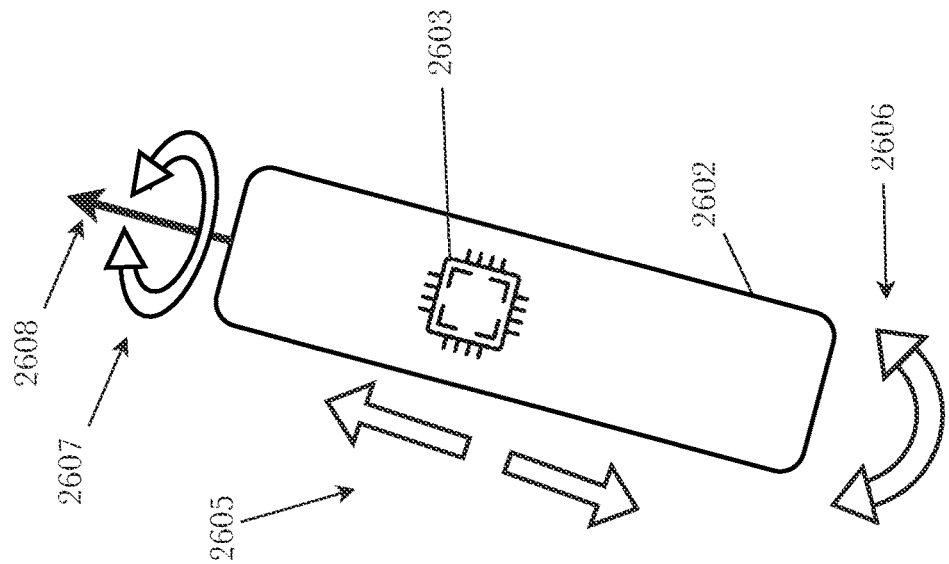
FIG. 26 shows an exemplary three-dimensional motion sensing controller for sexual stimulation devices.

FIG. 26 shows an exemplary three-dimensional motion sensing controller for sexual stimulation devices. In this embodiment, controller comprises a cylindrical shaft 2602, and an integrated control system 2603 comprising a microcontroller and an inertial measurement unit (IMU) configured to detect motions of shaft in three dimensions. In this embodiment, shaft 2602 can be waterproofed, allowing for control of sexual stimulation devices either through a natural stroking movement by gripping shaft with a hand and moving shaft 2605 in three-dimensional space with hand, or by insertion of shaft into a bodily orifice such as a mouth or vagina. This allows for control of sexual devices through natural hand movements or intercourse-type movements via insertion into a bodily orifice.

Control system 2603 is configured to detect motions of shaft in three dimensions, including linear movements 2605 along longitudinal axis 2608 of shaft 2602, tilting motions away from longitudinal axis 2608 of shaft 2602, and rotational movements about longitudinal axis 2608 of shaft 2602. Inertial measurement units (IMU) are collections of "sensors on a chip" containing built-in accelerometers, gyroscopes, and magnetic field sensors, plus a interfaces for receiving power and interfacing with microcontrollers. Each of sensors are typically 3-axis sensors capable of detection of movement with six degrees of freedom (i.e., linear movements in x, y, and z planes, and rotational movement about x, y, and z axes). IMUs are often described as having 3 axes of detection per sensor (e.g., 3 axes of detection if just an accelerometer is used, 6 axes of detection if both an accelerometer and gyroscope are used, etc.). Thus, control system is capable of detecting three-dimensional motions in any of six possible degrees of freedom. Note that shaft 2602 does not have to be cylindrical, and or cross-sectional shapes of shaft could be used (e.g., square, hexagonal, etc.). Note that motion sensors or than IMUs can be used (e.g., mercury tilt sensors, as one example).

Operation of the sexual stimulation device via the motion sensing controller can be done locally based on a wired or wireless connection between controller and device, or remotely based on connection between the controller and device through a local area network (LAN), wide area network (WAN), or via the Internet. Thus, the user of the controller and the user of the device may be the same person or different persons, and if different persons, may be co-located or remote from one another.

Figure 27:
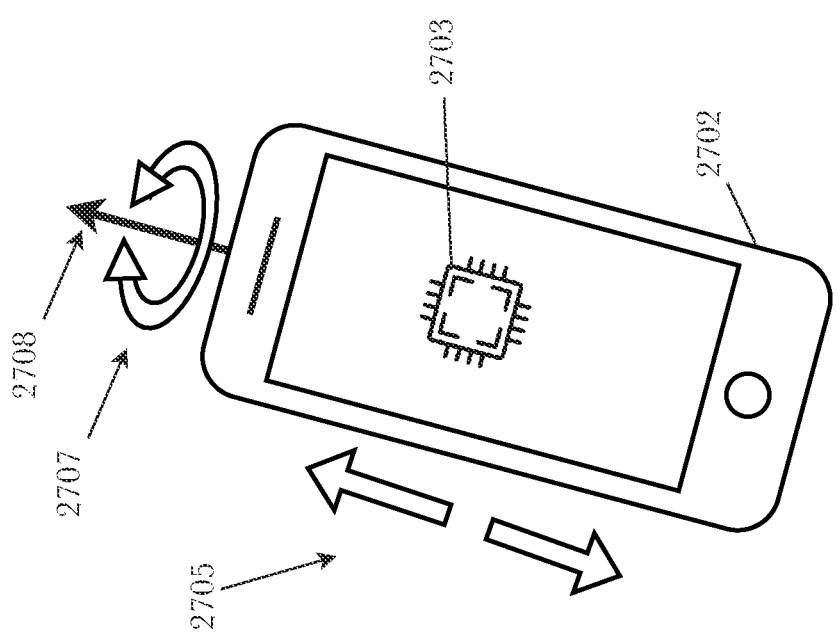
FIG. 27 shows an exemplary use of a mobile computing device as a three-dimensional motion sensing controller for sexual stimulation devices.

FIG. 27 shows an exemplary use of a mobile computing device as a three-dimensional motion sensing controller for sexual stimulation devices. In this embodiment, controller is a mobile computing device 2702 such as a smartphone comprising an inertial measurement unit (IMU) 2703 configured to detect motions of mobile computing device 2702 in three dimensions. This allows for control of sexual devices through natural hand movements by gripping mobile computing device 2702 and moving it in three dimensional space.

Mobile computing device 2702 with its integrated IMU 2703 is configured to detect motions of mobile computing device 2702 in three dimensions, including linear movements 2705 along longitudinal axis 2708 of mobile computing device 2702, tilting motions away from longitudinal axis 2708 of mobile computing device 2702, and rotational movements 2707 about longitudinal axis 2708 of mobile computing device 2702. In this embodiment, mobile computing device has its own control system (not shown) capable of interfacing with IMU. Inertial measurement units (IMU) are collections of "sensors on a chip" containing built-in accelerometers, gyroscopes, and magnetic field sensors, plus a interfaces for receiving power and interfacing with microcontrollers. Each of sensors are typically 3-axis sensors capable of detection of movement with six degrees of freedom (i.e., linear movements in x, y, and z planes, and rotational movement about x, y, and z axes). IMUs are often described as having 3 axes of detection per sensor (e.g., 3 axes of detection if just an accelerometer is used, 6 axes of detection if both an accelerometer and gyroscope are used, etc.). Thus, mobile computing device 2702 is capable of detecting three dimensional motions in any of six possible degrees of freedom.

Figure 28:
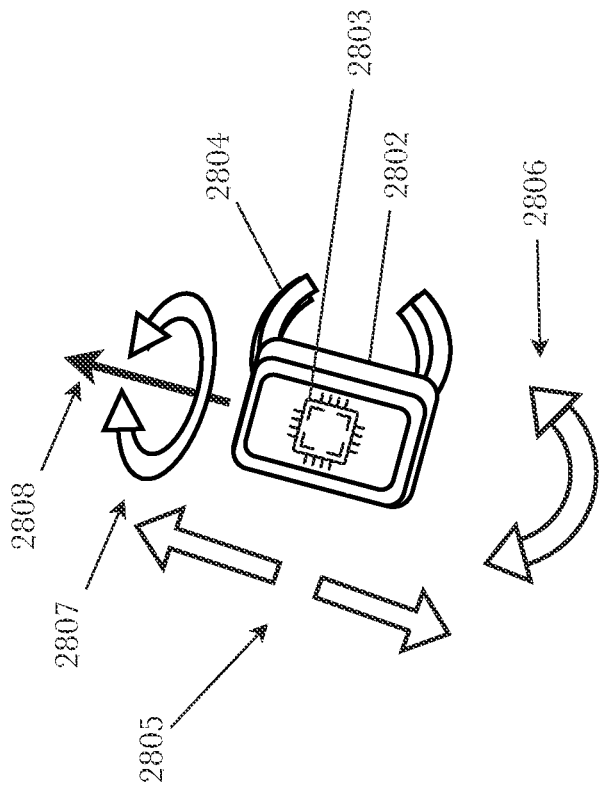
FIG. 28 shows an exemplary use of a smartwatch or fitness tracker as a three-dimensional motion sensing controller for sexual stimulation devices.

FIG. 28 shows an exemplary use of a wearable device as a three-dimensional motion sensing controller for sexual stimulation devices. In this embodiment, controller is a wearable device 2802 such as a smartwatch or fitness tracker comprising an inertial measurement unit (IMU) 2803 and a strap or other means for attaching device to a person or clothing 2804, and configured to detect motions of wearable device 2802 in three dimensions. This allows for control of sexual devices through natural hand movements by gripping wearable device 2802 and moving it in three-dimensional space or through natural body movements by moving portion of body or clothing to which wearable device 2802 is attached.

Wearable device 2802 with its integrated IMU 2803 is configured to detect motions of wearable device 2802 in three dimensions, including linear movements 2805 along longitudinal axis 2808 of wearable device 2802, tilting motions 2806 away from longitudinal axis 2808 of wearable device 2802, and rotational movements 2807 about longitudinal axis 2808 of wearable device 2802. In this embodiment, mobile computing device has its own control system (not shown) capable of interfacing with IMU. Inertial measurement units (IMU) are collections of "sensors on a chip" containing built-in accelerometers, gyroscopes, and magnetic field sensors, plus a interfaces for receiving power and interfacing with microcontrollers. Each of sensors are typically 3-axis sensors capable of detection of movement with six degrees of freedom (i.e., linear movements in x, y, and z planes, and rotational movement about x, y, and z axes). IMUs are often described as having 3 axes of detection per sensor (e.g., 3 axes of detection if just an accelerometer is used, 6 axes of detection if both an accelerometer and gyroscope are used, etc.). Thus, wearable device 2802 is capable of detecting three dimensional motions in any of six possible degrees of freedom.

Figure 29:
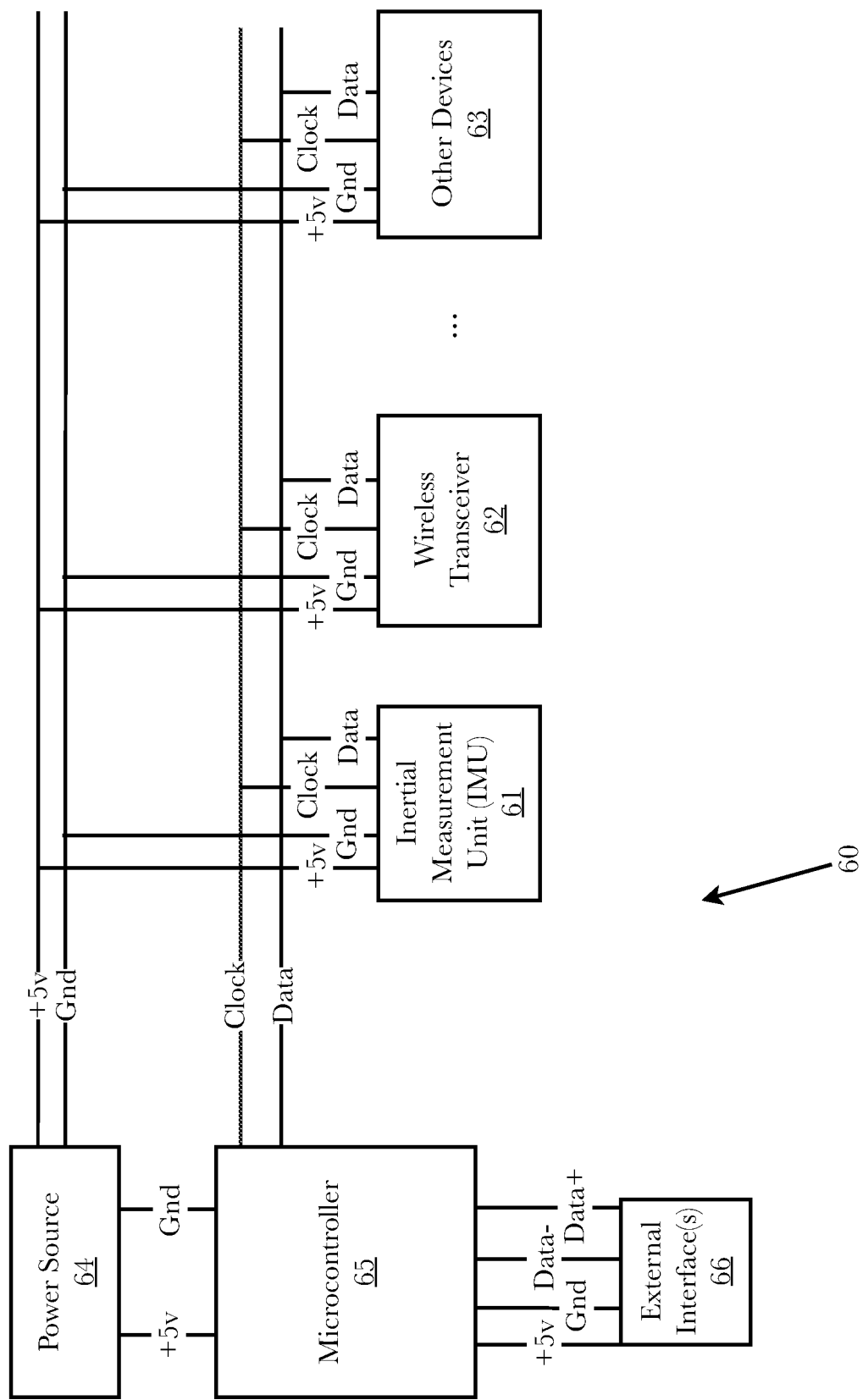
FIG. 29 is an exemplary system architecture diagram for a control unit for a motion sensing controller for sexual stimulation devices.

FIG. 29 is an exemplary system architecture diagram for a control system for a motion sensing controller for sexual stimulation devices. Control system detects manipulation of controller through its sensors and outputs signals corresponding to manipulations either as control signals for a compatible sexual stimulation device or as motion data to be converted into control signals for a compatible sexual stimulation device. In this example, control system 60 comprises a power source 64, a microcontroller 65, an external interface 66, and one or more input/output devices 61-63. Core of control system is a microcontroller 65, which is a small computing device with one or more processors, a memory, communications controllers, and one or more inputs and outputs. Microcontrollers 65 in this type of application are typically pre-programmed for intended use. Microcontroller 65 may have onboard power and/or may be powered by an external power source 64. Microcontroller 65 is used to receive input signals either from sensors 63 or computing devices, such as receiving signals from an inertial measurement unit (IMU) 61. Microcontroller 65 of this example contains an inter-integrated circuit bus (also known as I2C) which allows for fully addressable serial communication with slave devices such as IMU 61, a wireless transceiver 62, or input/output devices 63 using common wires for +5 v and ground (for power), a clock signal, and data. While not required, input/output devices 61-63 may also contain a communications controller allowing for I2C serial communications with microcontroller 65. In this example, microcontroller receives motion data from accelerometers, gyroscopes, magnetometers, and/or or motion sensors in IMU 61, translates motion data into control signals for a compatible sexual stimulation device, and transmits control signals to another compatible sexual stimulation device (or to another computing device for transmission to compatible sexual stimulation device) via wireless transmitter 62.

Although this example uses I2C serial communications protocol, any addressable communication protocol may be used, including serial and parallel communications protocols, such as serial to peripheral interface (SPI), universal asynchronous receiver-transmitter (UART), etc. In some embodiments, direct pinouts from microcontroller may be used instead of addressable communications protocols.

Operation of sexual stimulation device via motion sensing controller can be done locally based on a wired or wireless connection between controller and device, or remotely based on connection between the controller and device through a local area network (LAN), wide area network (WAN), or via the Internet. Thus, the user of the controller and the user of the device may be the same person or different persons, and if different persons, may be co-located or remote from one another. Further, in some embodiments, there may be either multiple controllers controlling a single sexual stimulation device, a single controller controlling multiple sexual stimulation devices, or multiple controllers controlling multiple sexual stimulation devices.

Hardware Architecture

Generally, techniques disclosed herein may be implemented on hardware or a combination of software and hardware. For example, they may be implemented in an operating system kernel, in a separate user process, in a library package bound into network applications, on a specially constructed machine, on an application-specific integrated circuit (ASIC), or on a network interface card.

Software/hardware hybrid implementations of at least some of aspects disclosed herein may be implemented on a programmable network-resident machine (which should be understood to include intermittently connected network-aware machines) selectively activated or reconfigured by a computer program stored in memory. Such network devices may have multiple network interfaces that may be configured or designed to utilize different types of network communication protocols. A general architecture for some of se machines may be described herein in order to illustrate one or more exemplary means by which a given unit of functionality may be implemented. According to specific aspects, at least some of features or functionalities of various aspects disclosed herein may be implemented on one or more general-purpose computers associated with one or more networks, such as for example an end-user computer system, a client computer, a network server or server system, a mobile computing device (e.g., tablet computing device, mobile phone, smartphone, laptop, or appropriate computing device), a consumer electronic device, a music player, or any or suitable electronic device, router, switch, or suitable device, or any combination thereof. In at least some aspects, at least some of features or functionalities of various aspects disclosed herein may be implemented in one or more virtualized computing environments (e.g., network computing clouds, virtual machines hosted on one or more physical computing machines, or or appropriate virtual environments).

Figure 30:
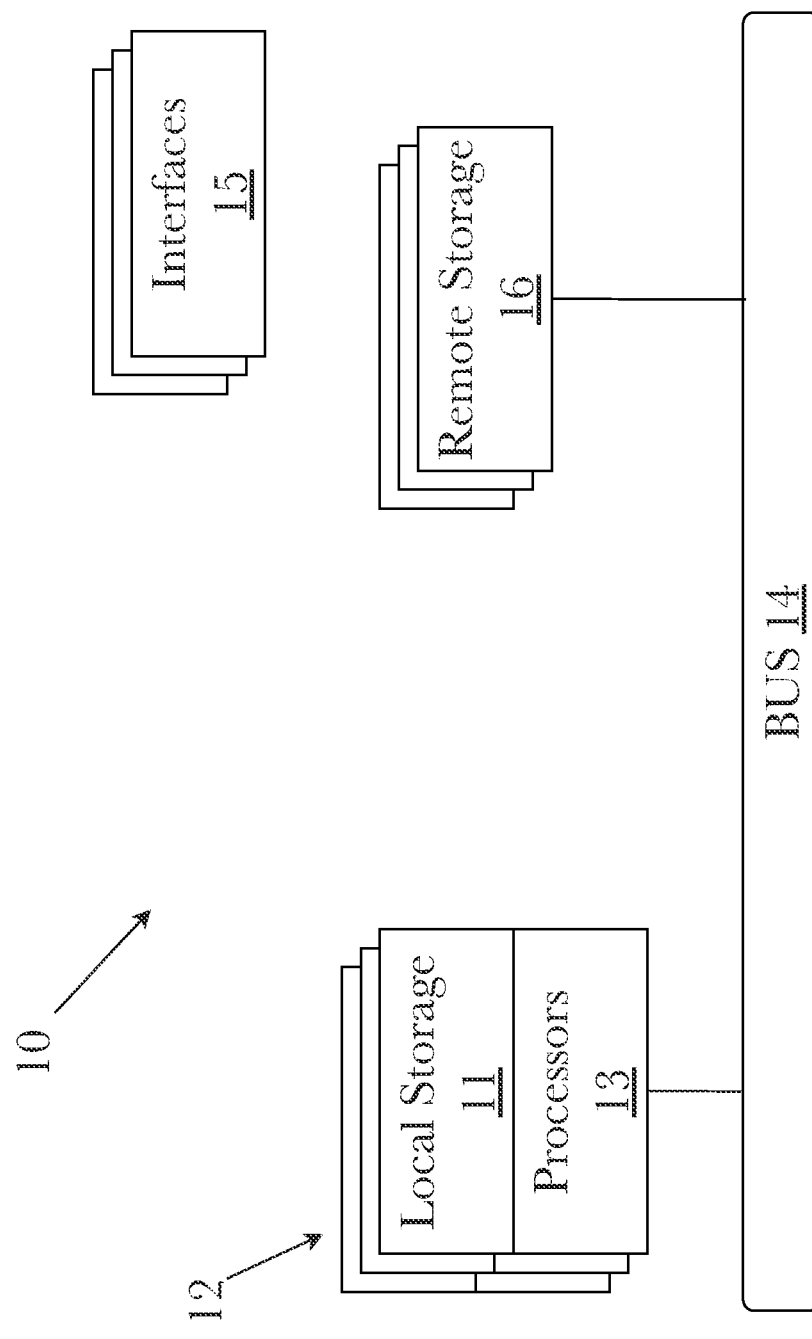
FIG. 30 is a block diagram illustrating an exemplary hardware architecture of a computing device.
Figure 3:
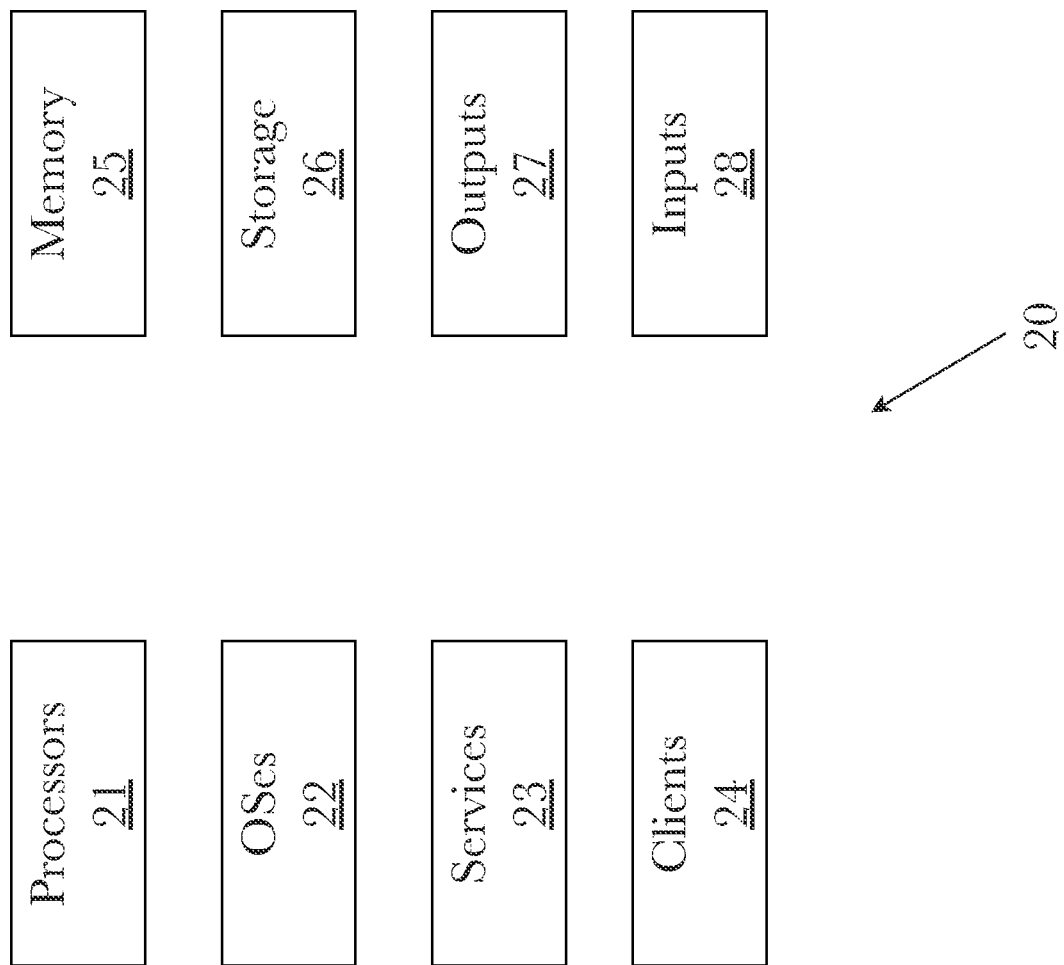

Referring now to FIG. 30, there is shown a block diagram depicting an exemplary computing device 10 suitable for implementing at least a portion of features or functionalities disclosed herein. Computing device 10 may be, for example, any one of computing machines listed in previous paragraph, or indeed any or electronic device capable of executing software- or hardware-based instructions according to one or more programs stored in memory. Computing device 10 may be configured to communicate with a plurality of or computing devices, such as clients or servers, over communications networks such as a wide area network a metropolitan area network, a local area network, a wireless network, Internet, or any or network, using known protocols for such communication, whether wireless or wired.

In one aspect, computing device 10 includes one or more central processing units (CPU) 12, one or more interfaces 15, and one or more busses 14 (such as a peripheral component interconnect (PCI) bus). When acting under control of appropriate software or firmware, CPU 12 may be responsible for implementing specific functions associated with functions of a specifically configured computing device or machine. For example, in at least one aspect, a computing device 10 may be configured or designed to function as a server system utilizing CPU 12, local memory 11 and/or remote memory 16, and interface(s) 15. In at least one aspect, CPU 12 may be caused to perform one or more of different types of functions and/or operations under control of software modules or components, which for example, may include an operating system and any appropriate applications software, drivers, and like.

CPU 12 may include one or more processors 13 such as, for example, a processor from one of Intel, ARM, Qualcomm, and AMD families of microprocessors. In some aspects, processors 13 may include specially designed hardware such as application-specific integrated circuits (ASICs), electrically erasable programmable read-only memories (EEPROMs), field-programmable gate arrays (FPGAs), and so forth, for controlling operations of computing device 10. In a particular aspect, a local memory 11 (such as non-volatile random access memory (RAM) and/or read-only memory (ROM), including for example one or more levels of cached memory) may also form part of CPU 12. However, re are many different ways in which memory may be coupled to system 10. Memory 11 may be used for a variety of purposes such as, for example, caching and/or storing data, programming instructions, and like. It should be further appreciated that CPU 12 may be one of a variety of system-on-a-chip (SOC) type hardware that may include additional hardware such as memory or graphics processing chips, such as a QUALCOMM SNAPDRAGON™ or SAMSUNG EXYNOS™ CPU as are becoming increasingly common in art, such as for use in mobile devices or integrated devices.

As used herein, term "processor" is not limited merely to those integrated circuits referred to in art as a processor, a mobile processor, or a microprocessor, but broadly refers to a microcontroller, a microcomputer, a programmable logic controller, an application-specific integrated circuit, and any or programmable circuit.

In one aspect, interfaces 15 are provided as network interface cards (NICs). Generally, NICs control sending and receiving of data packets over a computer network; or types of interfaces 15 may for example support or peripherals used with computing device 10. Among interfaces that may be provided are Ethernet interfaces, frame relay interfaces, cable interfaces, DSL interfaces, token ring interfaces, graphics interfaces, and like. In addition, various types of interfaces may be provided such as, for example, universal serial bus (USB), Serial, Ethernet, FIREWIRE™, THUNDERBOLT™, PCI, parallel, radio frequency (RF), BLUETOOTH™, near-field communications (e.g., using near-field magnetics), 802.11 (WiFi), frame relay, TCP/IP, ISDN, fast Ethernet interfaces, Gigabit Ethernet interfaces, Serial ATA (SATA) or external SATA (ESATA) interfaces, high-definition multimedia interface (HDMI), digital visual interface (DVI), analog or digital audio interfaces, asynchronous transfer mode (ATM) interfaces, high-speed serial interface (HSSI) interfaces, Point of Sale (POS) interfaces, fiber data distributed interfaces (FDDIs), and like. Generally, such interfaces 15 may include physical ports appropriate for communication with appropriate media. In some cases, they may also include an independent processor (such as a dedicated audio or video processor, as is common in art for high-fidelity A/V hardware interfaces) and, in some instances, volatile and/or non-volatile memory (e.g., RAM).

Although system shown in FIG. 30 illustrates one specific architecture for a computing device 10 for implementing one or more of aspects described herein, it is by no means only device architecture on which at least a portion of features and techniques described herein may be implemented. For example, architectures having one or any number of processors 13 may be used, and such processors 13 may be present in a single device or distributed among any number of devices. In one aspect, a single processor 13 handles communications as well as routing computations, while in or aspects a separate dedicated communications processor may be provided. In various aspects, different types of features or functionalities may be implemented in a system according to aspect that includes a client device (such as a tablet device or smartphone running client software) and server systems (such as a server system described in more detail below).

Regardless of network device configuration, system of an aspect may employ one or more memories or memory modules (such as, for example, remote memory block 16 and local memory 11) configured to store data, program instructions for general-purpose network operations, or information relating to functionality of aspects described herein (or any combinations of above). Program instructions may control execution of or comprise an operating system and/or one or more applications, for example. Memory 16 or memories 11, 16 may also be configured to store data structures, configuration data, encryption data, historical system operations information, or any or specific or generic non-program information described herein.

Because such information and program instructions may be employed to implement one or more systems or methods described herein, at least some network device aspects may include nontransitory machine-readable storage media, which, for example, may be configured or designed to store program instructions, state information, and like for performing various operations described herein. Examples of such nontransitory machine-readable storage media include, but are not limited to, magnetic media such as hard disks, floppy disks, and magnetic tape; optical media such as CD-ROM disks; magneto-optical media such as optical disks, and hardware devices that are specially configured to store and perform program instructions, such as read-only memory devices (ROM), flash memory (as is common in mobile devices and integrated systems), solid state drives (SSD) and "hybrid SSD" storage drives that may combine physical components of solid state and hard disk drives in a single hardware device (as are becoming increasingly common in art with regard to personal computers), memristor memory, random access memory (RAM), and like. It should be appreciated that such storage means may be integral and non-removable (such as RAM hardware modules that may be soldered onto a motherboard or otherwise integrated into an electronic device), or they may be removable such as swappable flash memory modules (such as "thumb drives" or or removable media designed for rapidly exchanging physical storage devices), "hot-swappable" hard disk drives or solid state drives, removable optical storage discs, or such removable media, and that such integral and removable storage media may be utilized interchangeably. Examples of program instructions include both object code, such as may be produced by a compiler, machine code, such as may be produced by an assembler or a linker, byte code, such as may be generated by for example a JAVA™ compiler and may be executed using a Java virtual machine or equivalent, or files containing higher level code that may be executed by computer using an interpreter (for example, scripts written in Python, Perl, Ruby, Groovy, or any or scripting language).

In some aspects, systems may be implemented on a standalone computing system. Referring now to FIG. 31, there is shown a block diagram depicting a typical exemplary architecture of one or more aspects or components thereof on a standalone computing system. Computing device 20 includes processors 21 that may run software that carry out one or more functions or applications of aspects, such as for example a client application 24. Processors 21 may carry out computing instructions under control of an operating system 22 such as, for example, a version of MICROSOFT WINDOWS™ operating system, APPLE macOS™ or iOS™ operating systems, some variety of Linux operating system, ANDROID™ operating system, or like. In many cases, one or more shared services 23 may be operable in system 20, and may be useful for providing common services to client applications 24. Services 23 may for example be WINDOWS™ services, user-space common services in a Linux environment, or any or type of common service architecture used with operating system 21. Input devices 28 may be of any type suitable for receiving user input, including for example a keyboard, touchscreen, microphone (for example, for voice input), mouse, touchpad, trackball, or any combination thereof. Output devices 27 may be of any type suitable for providing output to one or more users, where remote or local to system 20, and may include for example one or more screens for visual output, speakers, printers, or any combination thereof. Memory 25 may be random-access memory having any structure and architecture known in art, for use by processors 21, for example to run software. Storage devices 26 may be any magnetic, optical, mechanical, memristor, or electrical storage device for storage of data in digital form (such as those described above, referring to FIG. 30). Examples of storage devices 26 include flash memory, magnetic hard drive, CD-ROM, and/or like.

Figure 32:
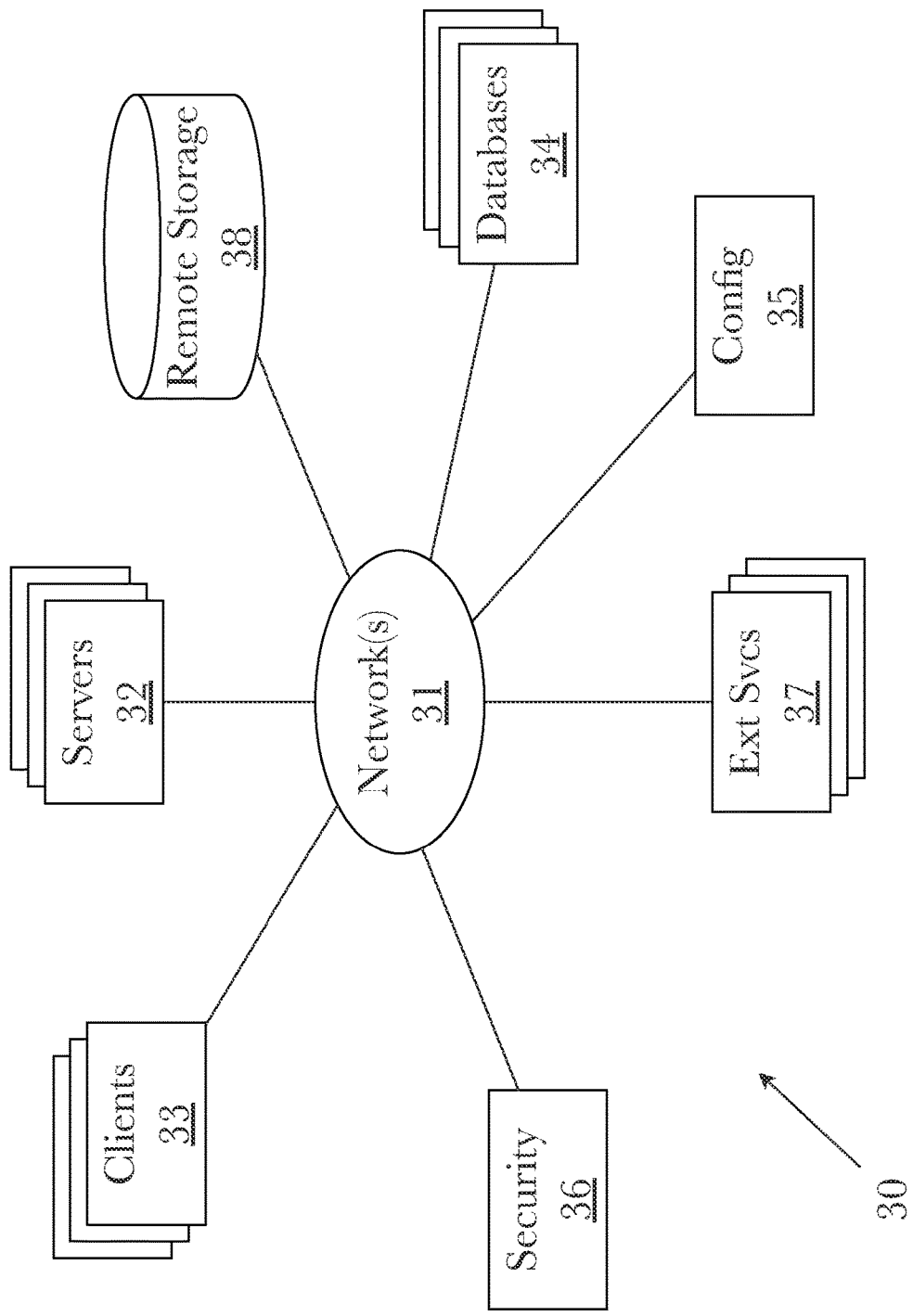
FIG. 32 is a block diagram showing an exemplary architectural arrangement of clients, servers, and external services.

In some aspects, systems may be implemented on a distributed computing network, such as one having any number of clients and/or servers. Referring now to FIG. 32, there is shown a block diagram depicting an exemplary architecture 30 for implementing at least a portion of a system according to one aspect on a distributed computing network. According to aspect, any number of clients 33 may be provided. Each client 33 may run software for implementing client-side portions of a system; clients may comprise a system 20 such as that illustrated in FIG. 31. In addition, any number of servers 32 may be provided for handling requests received from one or more clients 33. Clients 33 and servers 32 may communicate with one another via one or more electronic networks 31, which may be in various aspects any of Internet, a wide area network, a mobile telephony network (such as CDMA or GSM cellular networks), a wireless network (such as WiFi, WiMAX, LTE, and so forth), or a local area network (or indeed any network topology known in art; aspect does not prefer any one network topology over any or). Networks 31 may be implemented using any known network protocols, including for example wired and/or wireless protocols.

In addition, in some aspects, servers 32 may call external services 37 when needed to obtain additional information, or to refer to additional data concerning a particular call. Communications with external services 37 may take place, for example, via one or more networks 31. In various aspects, external services 37 may comprise web-enabled services or functionality related to or installed on hardware device itself. For example, in one aspect where client applications 24 are implemented on a smartphone or electronic device, client applications 24 may obtain information stored in a server system 32 in cloud or on an external service 37 deployed on one or more of a particular enterprise's or user's premises. In addition to local storage on servers 32, remote storage 38 may be accessible through network(s) 31.

In some aspects, clients 33 or servers 32 (or both) may make use of one or more specialized services or appliances that may be deployed locally or remotely across one or more networks 31. For example, one or more databases 34 in either local or remote storage 38 may be used or referred to by one or more aspects. It should be understood by one having ordinary skill in art that databases in storage 34 may be arranged in a wide variety of architectures and using a wide variety of data access and manipulation means. For example, in various aspects one or more databases in storage 34 may comprise a relational database system using a structured query language (SQL), while others may comprise an alternative data storage technology such as those referred to in art as "NoSQL" (for example, HADOOP CASSANDRA™, GOOGLE BIGTABLE™, and so forth). In some aspects, variant database architectures such as column-oriented databases, in-memory databases, clustered databases, distributed databases, or even flat file data repositories may be used according to aspect. It will be appreciated by one having ordinary skill in art that any combination of known or future database technologies may be used as appropriate, unless a specific database technology or a specific arrangement of components is specified for a particular aspect described herein. Moreover, it should be appreciated that term "database" as used herein may refer to a physical database machine, a cluster of machines acting as a single database system, or a logical database within an overall database management system. Unless a specific meaning is specified for a given use of term "database", it should be construed to mean any of se senses of word, all of which are understood as a plain meaning of term "database" by those having ordinary skill in art.

Similarly, some aspects may make use of one or more security systems 36 and configuration systems 35. Security and configuration management are common information technology (IT) and web functions, and some amount of each are generally associated with any IT or web systems. It should be understood by one having ordinary skill in art that any configuration or security subsystems known in art now or in future may be used in conjunction with aspects without limitation, unless a specific security 36 or configuration system 35 or approach is specifically required by description of any specific aspect.

Figure 33:
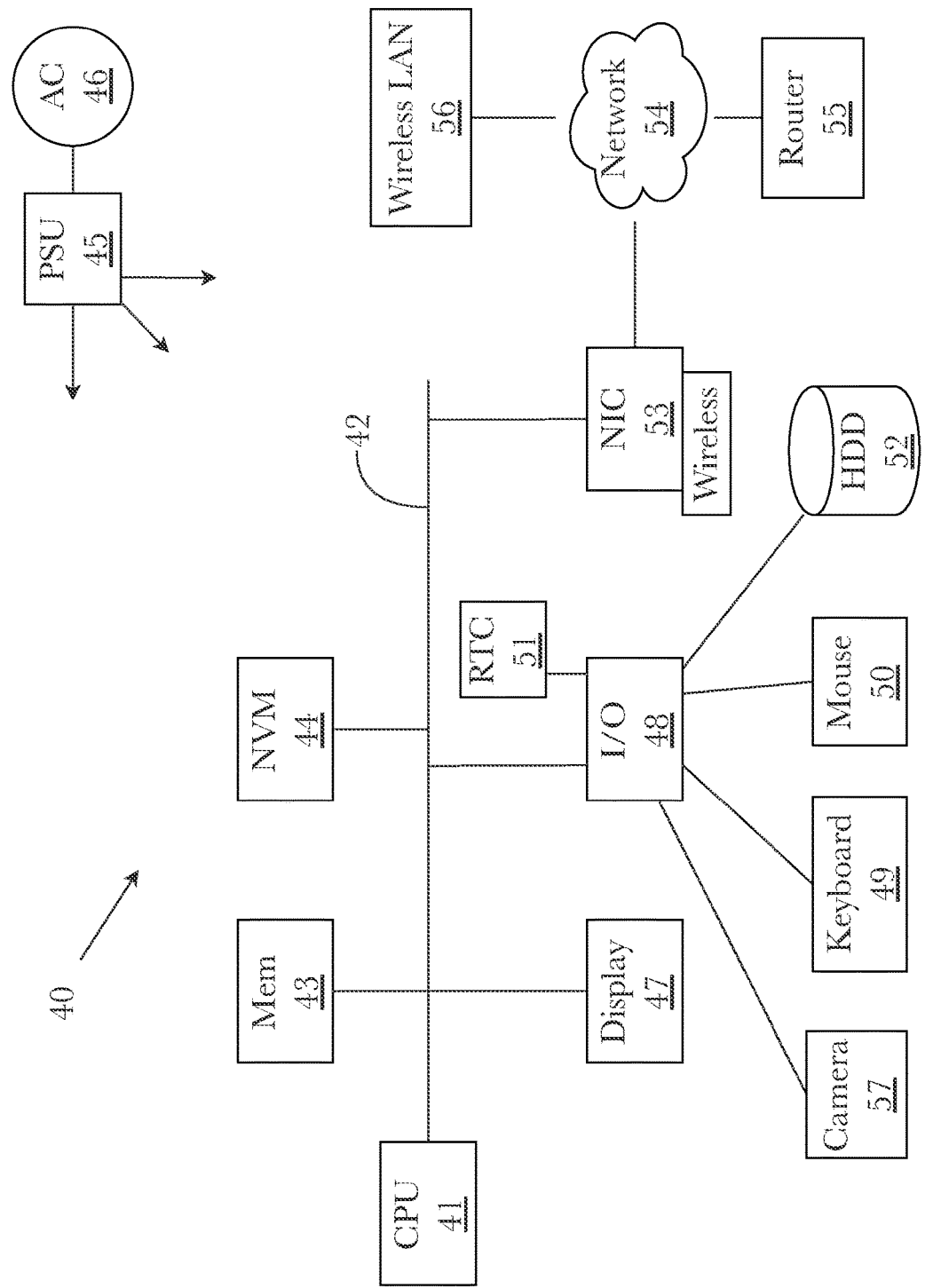
FIG. 33 is another block diagram illustrating an exemplary hardware architecture of a computing device.

FIG. 33 shows an exemplary overview of a computer system 40 as may be used in any of various locations throughout system. It is exemplary of any computer that may execute code to process data. Various modifications and changes may be made to computer system 40 without departing from broader scope of system and method disclosed herein. Central processor unit (CPU) 41 is connected to bus 42, to which bus is also connected memory 43, nonvolatile memory 44, display 47, input/output (I/O) unit 48, and network interface card (NIC) 53. I/O unit 48 may, typically, be connected to peripherals such as a keyboard 49, pointing device 50, hard disk 52, real-time clock 51, a camera 57, and or peripheral devices. NIC 53 connects to network 54, which may be Internet or a local network, which local network may or may not have connections to Internet. system may be connected to or computing devices through network via a router 55, wireless local area network 56, or any or network connection. Also shown as part of system 40 is power supply unit 45 connected, in this example, to a main alternating current (AC) supply 46. Not shown are batteries that could be present, and many or devices and modifications that are well known but are not applicable to specific novel functions of current system and method disclosed herein. It should be appreciated that some or all components illustrated may be combined, such as in various integrated applications, for example Qualcomm or Samsung system-on-a-chip (SOC) devices, or whenever it may be appropriate to combine multiple capabilities or functions into a single hardware device (for instance, in mobile devices such as smartphones, video game consoles, in-vehicle computer systems such as navigation or multimedia systems in automobiles, or integrated hardware devices).

In various aspects, functionality for implementing systems or methods of various aspects may be distributed among any number of client and/or server components. For example, various software modules may be implemented for performing various functions in connection with system of any particular aspect, and such modules may be variously implemented to run on server and/or client components.

The skilled person will be aware of a range of possible modifications of various aspects described above. Accordingly, present invention is defined by claims and or equivalents.

One or more different aspects may be described in the present application. Further, for one or more of the aspects described herein, numerous alternative arrangements may be described; it should be appreciated that these are presented for illustrative purposes only and are not limiting of the aspects contained herein or the claims presented herein in any way. One or more of the arrangements may be widely applicable to numerous aspects, as may be readily apparent from the disclosure. In general, arrangements are described in sufficient detail to enable those skilled in the art to practice one or more of the aspects, and it should be appreciated that other arrangements may be utilized and that structural, logical, software, electrical and other changes may be made without departing from the scope of the particular aspects. Particular features of one or more of the aspects described herein may be described with reference to one or more particular aspects or figures that form a part of the present disclosure, and in which are shown, by way of illustration, specific arrangements of one or more of the aspects. It should be appreciated, however, that such features are not limited to usage in the one or more particular aspects or figures with reference to which they are described. The present disclosure is neither a literal description of all arrangements of one or more of the aspects nor a listing of features of one or more of the aspects that must be present in all arrangements.

Headings of sections provided in this patent application and the title of this patent application are for convenience only, and are not to be taken as limiting the disclosure in any way.

Devices that are in communication with each other need not be in continuous communication with each other, unless expressly specified otherwise. In addition, devices that are in communication with each other may communicate directly or indirectly through one or more communication means or intermediaries, logical or physical.

A description of an aspect with several components in communication with each other does not imply that all such components are required. To the contrary, a variety of optional components may be described to illustrate a wide variety of possible aspects and in order to more fully illustrate one or more aspects. Similarly, although process steps, method steps, algorithms or the like may be described in a sequential order, such processes, methods and algorithms may generally be configured to work in alternate orders, unless specifically stated to the contrary. In other words, any sequence or order of steps that may be described in this patent application does not, in and of itself, indicate a requirement that the steps be performed in that order. The steps of described processes may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, does not imply that the illustrated process or any of its steps are necessary to one or more of the aspects, and does not imply that the illustrated process is preferred. Also, steps are generally described once per aspect, but this does not mean they must occur once, or that they may only occur once each time a process, method, or algorithm is carried out or executed. Some steps may be omitted in some aspects or some occurrences, or some steps may be executed more than once in a given aspect or occurrence.

When a single device or article is described herein, it will be readily apparent that more than one device or article may be used in place of a single device or article. Similarly, where more than one device or article is described herein, it will be readily apparent that a single device or article may be used in place of the more than one device or article.

The functionality or the features of a device may be alternatively embodied by one or more other devices that are not explicitly described as having such functionality or features. Thus, other aspects need not include the device itself Techniques and mechanisms described or referenced herein will sometimes be described in singular form for clarity. However, it should be appreciated that particular aspects may include multiple iterations of a technique or multiple instantiations of a mechanism unless noted otherwise. Process descriptions or blocks in figures should be understood as representing modules, segments, or portions of code which include one or more executable instructions for implementing specific logical functions or steps in the process. Alternate implementations are included within the scope of various aspects in which, for example, functions may be executed out of order from that shown or discussed, including substantially concurrently or in reverse order, depending on the functionality involved, as would be understood by those having ordinary skill in the art.

What is claimed is:

1. A male sexual stimulation system, comprising:
a male sexual stimulation device comprising:
- a first computing device comprising a first processor, a first memory, and a wireless receiver;
- a reciprocating linear motion driver;
- a gripper attached to the reciprocating linear motion driver via a bracket;
- a flexible sleeve which is inserted into the gripper and which has a means for affixing the sleeve to the gripper; and
- a rotational driving means attached to the gripper mechanism and configured to rotate the gripper under power of the rotational driving means independently of the linear motion of the bracket parallel to the longitudinal axis of the gripper; and a motion sensing controller configured to control the operation of the reciprocating linear motion driver, comprising:
- a second computing device comprising a second processor, a second memory, and a wireless transmitter; and
- a motion sensor comprising at least one of an accelerometer, a gyroscope, and a magnetometer.

2. The system of claim 1, wherein when the controller is moved in a reciprocal linear motion, the motion is detected by the motion sensor and a control signal corresponding to the motion is transmitted by the wireless transmitter to the wireless receiver, and the first computing device operates the reciprocating linear motion driver in accordance with the control signal.

3. The system of claim 1, wherein when the controller is moved in a reciprocal linear motion, the motion is detected by the motion sensor and motion data corresponding to the motion is transmitted by the wireless transmitter to the wireless receiver, and the first computing device converts the motion data into a control signal corresponding to the motion and operates the reciprocating linear motion driver in accordance with the control signal.

4. The device of claim 1, further comprising a second motor, actuator, or driver attached to the gripper mechanism and configured to rotate the gripper about a longitudinal axis parallel to the linear motion independently of the linear motion, wherein when the controller is moved in a rotating motion about a longitudinal axis of the controller, the rotating motion is detected by the motion sensor and a control signal corresponding to the rotating motion is transmitted by the wireless transmitter to the wireless receiver, and the first computing device operates the rotational motor, actuator, or rack and pinion mechanism in accordance with the control signal.

5. The device of claim 1, further comprising a second motor, actuator, or driver attached to the gripper mechanism and configured to rotate the gripper about a longitudinal axis parallel to the linear motion independently of the linear motion, wherein when the controller is moved in a rotating motion about a longitudinal axis of the controller, the rotating motion is detected by the motion sensor and motion data corresponding to the motion is transmitted by the wireless transmitter to the wireless receiver, and the first computing device converts the motion data into a control signal corresponding to the rotating motion and operates the rotational motor, actuator, or rack and pinion mechanism in accordance with the control signal.

6. The device of claim 1, further comprising:
one or more guide rods that guide the linear motion;
a pivot or joint installed at one end of the one or more guide rods; and
a second motor, driver, or actuator which changes the pivot angle of the one or more guide rods independently of the linear motion;
wherein the linear motion driver is affixed to the guide rods such that the linear motion remains parallel to the guide rods as the guide rods tilt; and
wherein when the controller is moved in a rotating motion away from a longitudinal axis of the controller, the rotating motion is detected by the motion sensor and a control signal corresponding to the rotating motion is transmitted by the wireless transmitter to the wireless receiver, and the first computing device operates the second motor, driver, or actuator in accordance with the control signal.

7. The device of claim 1, further comprising:
one or more guide rods that guide the linear motion;
a pivot or joint installed at one end of the one or more guide rods; and
a second motor, driver, or actuator which changes the pivot angle of the one or more guide rods independently of the linear motion;
wherein the linear motion driver is affixed to the guide rods such that the linear motion remains parallel to the guide rods as the guide rods tilt; and
wherein when the controller is moved in a rotating motion away from a longitudinal axis of the controller, the rotating motion is detected by the motion sensor and motion data corresponding to the rotating motion is transmitted by the wireless transmitter to the wireless receiver, and the first computing device converts the motion data into a control signal corresponding to the rotating motion and operates the second motor, driver, or actuator in accordance with the control signal.

* * * * *